US010988790B2

(12) United States Patent
Ochiai et al.

(10) Patent No.: US 10,988,790 B2
(45) Date of Patent: Apr. 27, 2021

(54) METHOD FOR PRODUCING STEVIOL AND STEVIOL GLYCOSIDE BY USING AOBGL11 HOMOLOG

(71) Applicant: SUNTORY HOLDINGS LIMITED, Osaka (JP)

(72) Inventors: Misa Ochiai, Kyoto (JP); Eiichiro Ono, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 113 days.

(21) Appl. No.: 16/303,849

(22) PCT Filed: May 25, 2017

(86) PCT No.: PCT/JP2017/019486

§ 371 (c)(1),
(2) Date: Nov. 21, 2018

(87) PCT Pub. No.: WO2017/204284

PCT Pub. Date: Nov. 30, 2017

(65) Prior Publication Data

US 2019/0203246 A1 Jul. 4, 2019

(30) Foreign Application Priority Data

May 25, 2016 (JP) ............................ JP2016-104404

(51) Int. Cl.

| | |
|---|---|
| ***C12P 19/56*** | (2006.01) |
| ***C12P 19/14*** | (2006.01) |
| ***C12N 15/09*** | (2006.01) |
| ***C12P 19/44*** | (2006.01) |
| ***C12N 5/10*** | (2006.01) |
| ***C12N 15/52*** | (2006.01) |
| ***C12N 15/74*** | (2006.01) |
| ***C12N 15/81*** | (2006.01) |
| ***C12N 15/82*** | (2006.01) |
| ***C12P 15/00*** | (2006.01) |
| ***C12N 9/24*** | (2006.01) |

(52) U.S. Cl.

CPC ................ *C12P 19/56* (2013.01); *C12N 5/10* (2013.01); *C12N 15/09* (2013.01); *C12N 15/52* (2013.01); *C12N 15/74* (2013.01); *C12N 15/81* (2013.01); *C12N 15/82* (2013.01); *C12P 15/00* (2013.01); *C12P 19/14* (2013.01); *C12P 19/44* (2013.01); *C12N 9/24* (2013.01); *C12Y 302/00* (2013.01)

(58) Field of Classification Search

None

See application file for complete search history.

(56) References Cited

U.S. PATENT DOCUMENTS

| | | | |
|---|---|---|---|
| 2013/0071887 | A1 | 3/2013 | Wehrli |
| 2018/0312892 | A1 | 11/2018 | Ochiai et al. |
| 2018/0327798 | A1 | 11/2018 | Ochiai et al. |

FOREIGN PATENT DOCUMENTS

| | | | | |
|---|---|---|---|---|
| CN | 102250990 A | | 11/2011 | |
| CN | 102827891 | * | 9/2012 | ............. C12P 15/00 |
| JP | H10-276775 A | | 10/1998 | |
| JP | 2013-516963 A | | 5/2013 | |
| KR | 10-2014-0070985 A | | 6/2014 | |
| WO | 2017/073716 A1 | | 5/2017 | |
| WO | 2017/073717 A1 | | 5/2017 | |

OTHER PUBLICATIONS

NCBI Accession No. EIT80529; beta-glucosidase-related glycosidase [Aspergillus oryzae 3.042] (Year: 2012).*

Purkayastha et al., "Steviol Glycosides in Purified Stevia Leaf Extract Sharing the Same Metabolic Fate", *Regulatory Toxicology and Pharmacology*, vol. 77, pp. 125-133 (2016).

Chaturvedula et al., "Structural Characterization of the Hydrolysis Products of the Sweet Principle Rebaudioside-F", *Asian Journal of Pharmaceutical and Clinical Research*, vol. 5, No. 1, pp. 83-85 (2012).

Extended European Search Report issued in EP Patent Application No. 17802870.0, dated Dec. 6, 2019.

"Database UniProt [online]", Accession No. Q2U8Y5, //www.uniprot.org/uniprot/Q2U8Y5.txt?version=59, May 11, 2016.

Ko et al., "Characterization of a Novel Steviol-producing β-glucosidase from *Pencillium decumbens* and Optimal Production of the Steviol", *Appl. Microbiol. Biotechnol.*, vol. 97, pp. 8151-8161 (2013).

Ko et al., "Mass Production of Rubusoside Using a Novel Stevioside-Specific β-Glucosidase from *Aspergillus aculeatus", Journal of Agriculture and Food Chemistry*, vol. 60, pp. 6210-6216 (2012).

Langston et al., "Substrate Specificity of *Aspergillus oryzae* Family 3 β-Glucosidase", *Biochimica et Biophysica Acta*, vol. 1764, pp. 972-978 (2006).

Miyashiro, "Purification and Properties of Stevioside Hydrolyzing Enzyme from Raw Soy Sauce", *Nippon Shokuhin Kogyo Gakkaishi*, vol. 37, No. 5, pp. 369-374 (1990), including an English-language abstract.

Okamoto et al., "Purification and Some Properties of a β-Glucosidase from *Flavobacterium johnsonae", Biosci. Biotechnol. Biochem.*, vol. 64, No. 2, pp. 333-340 (2000).

Sakamoto et al., "Quantitative Analysis of Stevioside", Yakugaku Zasshi, 95 (12), pp. 1507-1510 (1975), including an English-language abstract.

Bennett et al., "Biosynthesis of Steviol (-)-Kaurene", *Phytochemistry*, vol. 6, pp. 1107-1110 (1967).

(Continued)

*Primary Examiner* — Anand U Desai

(74) *Attorney, Agent, or Firm* — Greenblum & Bernstein, P.L.C.

(57) ABSTRACT

There has been a demand for a new method for producing a steviol glycoside and steviol. The present invention provides a method for producing a steviol glycoside and/or steviol, the method comprising a step of breaking bonds of steviol glycoside: a glucosidic bond at position 13; a glucosyl ester bond at position 19; and/or a glycosidic bond in a side chain (excluding a rhamnoside bond).

15 Claims, 14 Drawing Sheets

Specification includes a Sequence Listing.

(56) References Cited

OTHER PUBLICATIONS

Ma et al., "Biological Conversion of Stevioside to Steviol by *Aspergillus aculeatus* and the Purification of Rebaudioside A", *Acta Microbiologica Sinica*, vol. 54, No. 1, pp. 62-68 (2014), including an English-language abstract.

Kasai et al., "Sweet Diterpene-Glycosides of Leaves of Stevia rebaudiana Bertoni—Synthesis and Structure-Sweetness Relationship of Rebaudiosides-A, -D, -E and Their Related Glycosides--", *The Chemical Society of Japan*, (5), pp. 726-735 (1981), including an English-language abstract.

Kaya et al., "Isoflavone Aglycones Production from Isoflavone Glycosides by Display of Beta-glucosides from *Aspergillus oryzae* on Yeast Cell Surface", *Appl. Microbiol. Biotechnol.*, vol. 79, pp. 51-60 (2008).

International Search Report issued in PCT/JP2017/019486, dated Aug. 15, 2017.

* cited by examiner

FIG. 10A

1 ... 100
AOBGL11G ...TAAGTCAAAAACCCACGATGGCAAGAGAA
AOBGL11CDS

101 ... 200
AOBGL11G AAGAAAATGCTAAGAATCCCAGC...
AOBGL11CDS

201 ... 300
AOBGL11G
AOBGL11CDS

301 ... 400
AOBGL11G
AOBGL11CDS

401 ... 500
AOBGL11G
AOBGL11CDS

501 ... 600
AOBGL11G
AOBGL11CDS

601 ... 700
AOBGL11G
AOBGL11CDS

701 ... 800
AOBGL11G
AOBGL11CDS

801 ... 900
AOBGL11G
AOBGL11CDS

901 ... 1000
AOBGL11G
AOBGL11CDS

1001 ... 1100
AOBGL11G
AOBGL11CDS

1101 ... 1200
AOBGL11G
AOBGL11CDS

1201 ... 1300
AOBGL11G
AOBGL11CDS

1301 ... 1400
AOBGL11G
AOBGL11CDS

1401 ... 1500
AOBGL11G
AOBGL11CDS

1501 ... 1600
AOBGL11G
AOBGL11CDS

1601 ... 1700
AOBGL11G
AOBGL11CDS

Figure 11A:
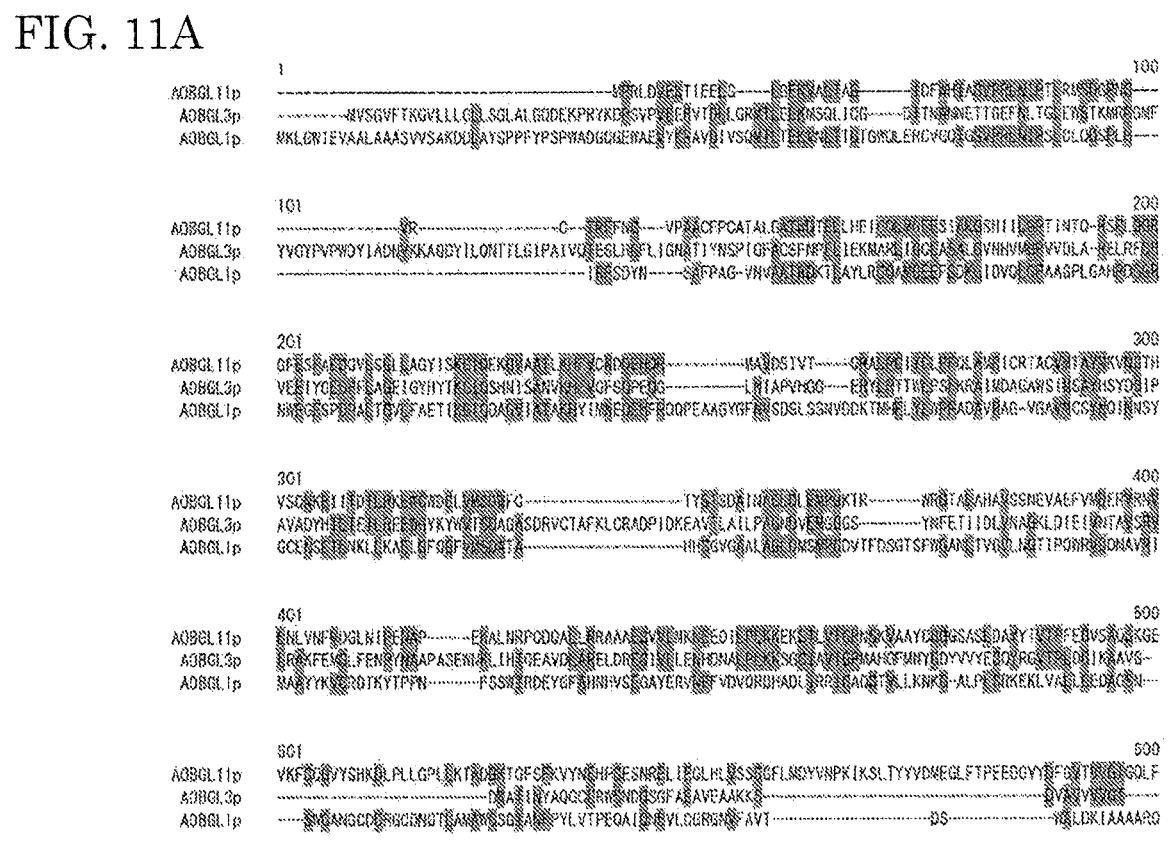

AOBGL11p [illegible]
AOBGL3p [illegible]
AOBGL1p [illegible]

101 … 200

AOBGL11p [illegible]
AOBGL3p [illegible]
AOBGL1p [illegible]

201 … 300

AOBGL11p [illegible]
AOBGL3p [illegible]
AOBGL1p [illegible]

301 … 400

AOBGL11p [illegible]
AOBGL3p [illegible]
AOBGL1p [illegible]

401 … 500

AOBGL11p [illegible]
AOBGL3p [illegible]
AOBGL1p [illegible]

501 … 600

AOBGL11p [illegible]
AOBGL3p [illegible]
AOBGL1p [illegible]

FIG. 11B

```
          601                                                                                                  700
AOBGL11p  1DGE[illegible]VD[illegible]TK[illegible]RO[illegible]S[illegible]FFGSA[illegible]V[illegible]EKGSKELKAGGTYKVLFGFGTAPTSDLDTRGVVVFGPGGFRFGASRRVGQEELISNAVKLASEAEQVVVFAGLT
AOBGL3p   ----------[illegible]RD[illegible]KELW[illegible]G[illegible]VAT[illegible]G----------------------------------------
AOBGL1p   ASVS[illegible]FV[illegible]DS----[illegible]ECY[illegible]SVDGN[illegible]------------------------------G----------

          701                                                                                                  800
AOBGL11p  SESET[illegible]GY[illegible]DHRD[illegible]PPGS[illegible]EN[illegible]SRVL[illegible]VNP[illegible]RAN----K[illegible]I[illegible]VRL[illegible]V
AOBGL3p   ------[illegible]IVD[illegible]SLS[illegible]VGADAPL[illegible]AIIDTGVP[illegible]LS[illegible]KRI[illegible]E[illegible]LSN--[illegible]VGDFY[illegible]SEQG[illegible]AL[illegible]SVS[illegible]HSVG[illegible]I[illegible]Y
AOBGL1p   ----------[illegible]WTT[illegible]KNG[illegible]NVV[illegible]TAAMNC[illegible]I[illegible]HSVG[illegible]LIDEWYDHP[illegible]VTGI[illegible]GAK[illegible]RGKTRESYG[illegible]PL

          801                                                                                                  900
AOBGL11p  NFRSER-------GRVL[illegible]GED[illegible]YVC[illegible]Y[illegible]E[illegible]VDLA[illegible]LF[illegible]TETT[illegible]PEK-----------------------
AOBGL3p   DYLNSAREI[illegible]DAGYI[illegible]SN[illegible]TLEFGHQ[illegible]ALG[illegible]PKA[illegible]SS[illegible]YGAVK[illegible]DK[illegible]-------------------
AOBGL1p   VKDANNGN-[illegible]APGSDFTG[illegible]F[illegible]IQ[illegible]HFD[illegible]ET[illegible]I[illegible]VQPL[illegible]ASRYTPTSGNTEAAKNFGEIGDASEYVYPEGLERIHEFIYPW

          901                                                                                                  1000
AOBGL11p  ---------------------------------[illegible]QYEE[illegible]GEP------------I[illegible]ATYT[illegible]-AR[illegible]APPATE[illegible]R[illegible]
AOBGL3p   ------------------------------------VTEADT--------------V[illegible]DATREGI[illegible]VDEVAS[illegible]VV[illegible]L[illegible]VIPA
AOBGL1p   INSTDLKASSGDENYGNEDSKYIPEGATDGSAQ[illegible]RLPA[illegible]GAGGNPGLYEDLFR[illegible]-DE[illegible]SLGGP--[illegible]KVV[illegible]RK[illegible]RIH[illegible]

          1001                                                  1060
AOBGL11p  [illegible]VVEKKLATS[illegible]FDGN[illegible]WAS[illegible]EYE[illegible]TGTG[illegible]SV[illegible]KS[illegible]TKVEKTRYWLGL
AOBGL3p   [illegible]TK[illegible]F[illegible]KYG[illegible]GL[illegible]N---V[illegible]Y[illegible]AFG[illegible]SEDIRGNATFYV[illegible]--------
AOBGL1p   S[illegible]EAVWTTT[illegible]TRR[illegible]AN[illegible]DVSAGDWT[illegible]TPYPKTIYVGN[illegible]RKLF[illegible]GA[illegible]LPKA[illegible]---------
```

FIG. 12A

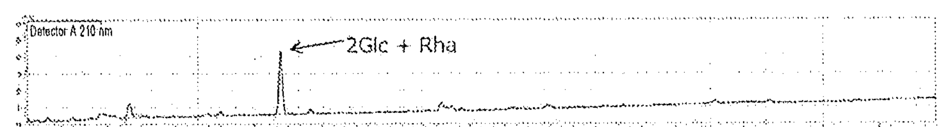

FIG. 12B

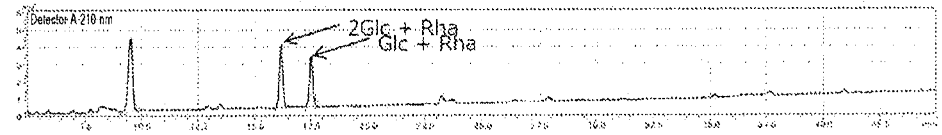

FIG. 12C

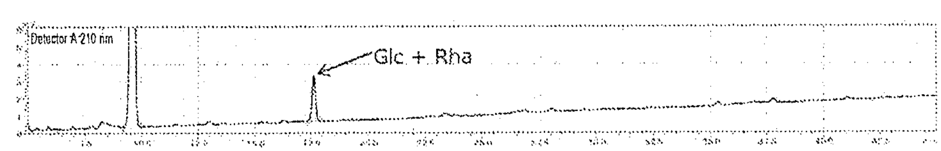

FIG. 12D

Detector A 210 nm

Glc + Rha

FIG. 13A
Detector A 210 nm
Only substrate
rebF
rebC
FIG. 13B
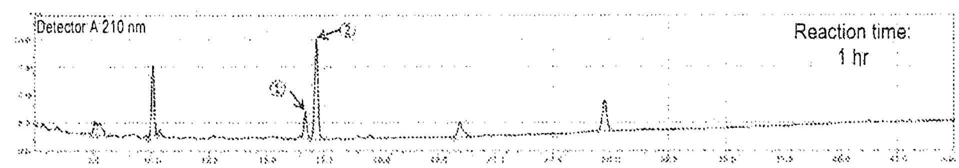
FIG. 13C
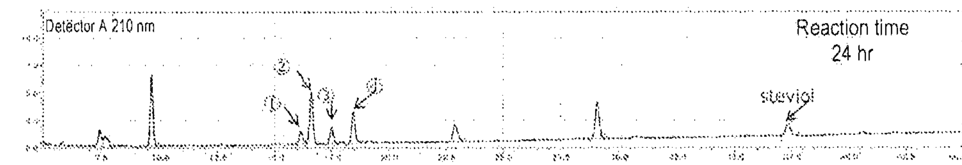
①2Glc + Rha、② 2Glc + Xly、 ③ Glc + Rha、
④ Glc + Xly

METHOD FOR PRODUCING STEVIOL AND STEVIOL GLYCOSIDE BY USING AOBGL11 HOMOLOG

TECHNICAL FIELD

The present invention relates to a method for producing steviol and a steviol glycoside.

BACKGROUND ART

The leaves of *Stevia rebaudiana* of the Asteraceae family contain a secondary metabolite called "steviol" which is a kind of diterpenoid. Steviol glycosides, which are products of the addition of sugars to steviol, include those having sweetness about 300 times higher than that of sucrose. Such steviol glycosides are used as non-caloric sweeteners in the food industry. Obesity is becoming more of a serious social issue on an international scale, and non-caloric sweeteners are increasingly demanded from the viewpoint of promotion of health and reduction of medical cost. Currently, aspartame and acesulfame potassium, which are artificially-synthesized amino acid derivatives, are used as artificial sweeteners. However, naturally-occurring non-caloric sweeteners such as steviol glycosides are expected to be safer and gain more public acceptance.

Among steviol glycosides, stevioside (stv) is a compound in which three glucose units are added to steviol, and is contained in the largest amount in the leaves of common *Stevia rebaudiana*. Stevioside (stv) has a degree of sweetness about 300 times higher than that of sucrose, but has slightly bitter taste. Rebaudioside A (rebA), which is another steviol glycoside, is a compound in which four glucose units are added to steviol, and has a degree of sweetness about 400 times higher than that of sucrose. Stevioside and rebaudioside A are primary substances responsible for the sweetness of *Stevia rebaudiana*. There are also known glycosides such as rebaudioside D (rebD) in which five glucose units are added to steviol and rebaudioside M (rebM) in which six glucose units are added to steviol. It is also known that *Rubus suavissimus* contains rubusoside (rub) in which one glucose unit is added at each of the 13 and 19 positions of steviol and that this rubusoside is a primary sweet component of *Rubus suavissimus*. In addition to the above glycosides, glycosides considered to be reaction intermediates and analogs differing in the type of sugar are known to exist (FIG. 1).

Meanwhile, steviol is known to have, for example, improving effect on cognitive function.

If an enzyme acting only on a specific glycoside bond in steviol glycosides can be used, selective production of a specific glycoside or elimination of an unnecessary glycoside will become possible. This will bring a lot of merits such as facilitating the improvement in taste of *Stevia rebaudiana* extracts or the purification of a specific steviol glycoside.

Furthermore, steviol is also useful for the step of using steviol as a starting material and glycosylating the steviol through the use of yeast or the like to obtain a steviol glycoside. Yeast is capable of taking up steviol into its cells by adding the steviol into a culture medium. Therefore, when yeast caused to express steviol glycosidase gene in its cells is cultured in a culture medium containing steviol, the yeast can take up the steviol into its cells and glycosylate the steviol. On the other hand, it is known that yeast can neither take up a steviol glycoside into its cells nor further perform glycosylation even if the steviol glycoside is added into a culture medium. As stated above, steviol is more desirable than steviol glycosides for cellular uptake by yeast. Thus, there is a demand for steviol.

An enzyme activity to hydrolyze steviol glycosides has been reported to be observed in some organism species. In particular, concerning the production of steviol glycoside-hydrolyzing enzymes by filamentous fungi of the genus *Aspergillus*, it has been reported that raw soy sauce has an activity to hydrolyze stevioside into rubusoside (Non Patent Literature 1) and that a pectinase enzyme agent, hesperidinase enzyme agent, and takadiastase enzyme agent have an activity to hydrolyze stevioside into steviol (Non Patent Literatures 2 to 4). A method has also been reported in which steviol is produced from stevioside by the combined use of a pectinase enzyme agent from filamentous fungi of the genus *Aspergillus* and an enzyme agent from *Helix pomatia* (Patent Literature 1). Viscozyme L (novozyme), an enzyme agent from *Aspergillus aculeatus*, has been described to have an activity to hydrolyze stevioside into rubusoside and then into steviol monoglycosyl ester (Non Patent Literature 5). Additionally, an extract obtained from *Aspergillus aculeatus* by solid culture has been described to have an activity to convert stevioside into steviol (Non Patent Literature 6).

As stated above, filamentous fungi of the genus *Aspergillus*, including koji mold, have been suggested to have an enzyme gene having steviol glycoside-hydrolyzing activity. However, there has been no report of any enzyme responsible for enzyme activity or gene encoding the enzyme.

It has been reported that the β-glucosidase of the glycoside hydrolase (GH) family 3 encoded by the AO090009000356 gene of koji mold hydrolyzes disaccharides with a β-glucoside bond (Non Patent Literature 7). Specifically, its specificity for hydrolysis is the highest for laminaribiose with a β-1,3 linkage, followed by β-gentiobiose with a β-1,6 linkage, cellobiose with a β-1,4 linkage, and sophorose with a β-1,2 linkage. However, there has been no report on whether the β-glucosidase has an activity to hydrolyze terpene glycosides typified by steviol glycosides.

Some other organisms have also been reported to have an activity to hydrolyze steviol glycosides. For example, it has been disclosed that bacteria of the genus *Clavibacter* have an enzyme that decomposes the glucosyl ester bond at the 19 position of rubusoside but does not decompose the glucoside bond at the 13 position (Patent Literature 2). Additionally, it has been reported that *Flavobacterium johnsoniae*-derived β-glucosidase has an activity to decompose steviol glycosides (an activity to hydrolyze the β-glucoside bond at the 13 position and the glucosyl ester bond at the 19 position) (Non Patent Literature 8).

It has been reported that *Penicillium decumbens*-derived naringinase includes an enzyme hydrolyzing stevioside through rubusoside, steviolbioside, and steviol monoglucoside into steviol, and this enzyme is a protein having a molecular weight of 121 kDa and is stable at a pH of 2.3 to 6.0 and a temperature of 40 to 60° C. (Non Patent Literature 9).

Although these have been found to have an activity to hydrolyze steviol glycosides, the gene responsible for this activity has not been identified.

Moreover, koji mold contains a large number of genes considered to encode GH3 family or GH5 family enzymes having β-glucosidase-like activity, and thus, even if an enzyme activity can be detected, it is not easy to determine which gene is responsible for the activity.

CITATION LIST

Patent Literature

Patent Literature 1: National Publication of International Patent Application No. 2013-516963

Patent Literature 2: Japanese Patent Laid-Open No. 10-276775

Patent Literature 3: Japanese Patent Laid-Open No. 10-276775

Non Patent Literature

Non Patent Literature 1: Journal of the Japanese Society for Food Science and Technology, vol. 37, No. 5, 369-374 (1990)

Non Patent Literature 2: Phytochemistry, 6, 1107 (1967)

Non Patent Literature 3: Journal of the Pharmaceutical Society of Japan, 95, 1507 (1975)

Non Patent Literature 4: Journal of the Chemical Society of Japan, 1981, 726 (1981)

Non Patent Literature 5: J. Agric. Food Chem., 60, 6210-6216(2012)

Non Patent Literature 6: Wei Sheng Wu Xue Bao, 54(1), 62-68(2014)

Non Patent Literature 7: Biochim Biophys Acta., 1764 972-978 (2006)

Non Patent Literature 8: Biosci. Biotechnol. Biochem., 64(2), 333-340, 2000

Non Patent Literature 9: Appl. Microbiol. Biotechnol., 97, 8151-8161

SUMMARY OF INVENTION

Technical Problem

Under the foregoing circumstances, there is a need for a novel method of producing Steviol and Steviol glycosides.

Solution to Problem

The present inventors conducted extensive research to solve the aforementioned problem, and found that the koji mold *Aspergillus oryzae* var. *Brunneus*-derived glycoside hydrolase homolog (GH3 family) protein AOBGL11p encoded by AOBGL11 gene or its homolog gene has an activity to hydrolyze steviol glycosides. The present inventors further found that the protein AOBGL11p cleaves a glucoside bond and glucosyl ester bond of a steviol glycoside. That is, the present inventors have found that AOBGL11p has an activity to cleave an O-glucoside bond at the 13 position, glucosyl ester bond at the 19 position, and glycoside bond within a side chain, which are linking sites between steviol and sugars in the steviol glycoside, on a monosaccharide basis, thus completing the present invention.

Additionally, the present inventors have found that hydrolysis reaction of a branched trisaccharide or sophorose linked to the 13 position, or hydrolysis reaction of a branched trisaccharide linked to the 19 position is suppressed in a steviol glycoside by selecting reaction conditions. The present inventors have also found that a glucosyl ester bond at the 19 position is preferentially cleaved over glucoside bond at the 13 position.

In summary, the present invention is as set forth below.

[2]

A method of producing steviol and/or a second steviol glycoside comprising reacting a protein selected from the group consisting of proteins (a) to (c) shown below with a first steviol glycoside, thereby hydrolyzing at least one of glucoside bond at the 13 position, glucosyl ester bond at the 19 position, and glycoside bond within a side chain of said first steviol glycoside, wherein said first and second steviol glycosides differ from each other:

(a) a protein consisting of the amino acid sequence of SEQ ID NO: 2;

(b) a protein consisting of an amino acid sequence wherein 1 to 83 amino acids have been deleted, substituted, inserted, and/or added in the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of the first steviol glycoside; and (c) a protein having an amino acid sequence having a sequence identity of 90% or more to the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of the first steviol glycoside.

[2]

The method according to [1] above, wherein the first steviol glycoside is selected from the group consisting of steviolmonoside, steviol monoglucosyl ester, rubusoside, steviolbioside, stevioside, rebaudioside B, rebaudioside A, rebaudioside C, rebaudioside D, rebaudioside E, rebaudioside F, rebaudioside M, dulcoside A, steviol glycoside B, steviol glycoside C, and steviol glycoside D.

[3]

The method according to [1] or [2] above, wherein the second steviol glycoside is selected from the group consisting of steviolmonoside, steviolbioside, rebaudioside B, steviol glycoside A, steviol glycoside B, steviol glycoside C, and steviol glycoside D.

[4]

The method according to any one of [1] to [3] above, wherein the reaction with the first steviol glycoside is performed in the presence of an organic solvent.

[5]

The method according to [4] above, wherein the organic solvent is acetonitrile.

[6]

The method according to any one of [1] to [5] above, comprising preferentially cleaving a glucosyl ester bond at the 19 position or glycoside bond (except for rhamnoside bond) within a side chain at the 19 position of the first steviol glycoside over glucoside bond at the 13 position or glycoside bond (except for rhamnoside bond) within a side chain at the 13 position thereof.

[7]

The method according to any one of [1] to [6] above, wherein the first steviol glycoside is a steviol glycoside wherein a branched trisaccharide, disaccharide, or glucose monosaccharide is linked through glucoside bond to the 13 position, and/or a branched trisaccharide, disaccharide, or glucose monosaccharide is linked through a glucosyl ester bond to the 19 position, and the hydrolysis of the first steviol glycoside comprises any one or more steps selected from the group consisting of the following steps (1) to (5):

(1) preferentially cleaving glycoside bond (except for rhamnoside bond) within the disaccharide or the glucoside bond or glucosyl ester bond of the glucose monosaccharide over the branched trisaccharide;

(2) preferentially cleaving glucose when xylose and glucose, or rhamnose and glucose are further linked to glucose linked to aglycone;

(3) preferentially cleaving glycoside bond (except for rhamnoside bond) within the branched trisaccharide at the 19 position over glycoside bond (except for rhamnoside bond) within the branched trisaccharide at the 13 position;

(4) preferentially cleaving glycoside bond (except for rhamnoside bond) within the branched trisaccharide or disaccharide at the 19 position and the glucosyl ester bond of the glucose monosaccharide at the 19 position over glycoside bond (except for rhamnoside bond) within the disaccharide at the 13 position; and (5) preferentially cleaving the glucosyl ester bond of the glucose monosaccharide at the 19 position over the glucoside bond of the glucose monosaccharide at the 13 position.

[8]

A method of producing steviol and/or a second steviol glycoside comprising contacting an enzyme from a non-human transformed cell obtained by introducing, into a host cell, a polynucleotide selected from the group consisting of polynucleotides (a) to (e) shown below, with a first steviol glycoside, thereby hydrolyzing glucoside bond at the 13 position, glucosyl ester bond at the 19 position, and/or glycoside bond (except for rhamnoside bond) within a side chain of said first steviol glycoside, wherein said first and second steviol glycosides differ from each other:

(a) a polynucleotide consisting of the nucleotide sequence of SEQ ID NO: 1;

(b) a polynucleotide encoding a protein consisting of the amino acid sequence of SEQ ID NO: 2;

(c) a polynucleotide encoding a protein consisting of an amino acid sequence wherein 1 to 83 amino acids have been deleted, substituted, inserted, and/or added in the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of the first steviol glycoside;

(d) a polynucleotide encoding a protein having an amino acid sequence having a sequence identity of 90% or more to the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of the first steviol glycoside; and (e) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to hydrolyze at least one of glucoside bond at the 13 position, glucosyl ester bond at the 19 position, and glycoside bond (except for rhamnoside bond) within a side chain of the first steviol glycoside.

[9]

The method according to [8] above, wherein the polynucleotide is inserted into an expression vector.

[10]

The method according to [8] or [9] above, wherein the transformed cell is transformed koji mold, transformed yeast, a transformed bacterium, or a transformed plant.

[11]

The method according to any one of [8] to [10] above, wherein the first steviol glycoside is selected from the group consisting of steviolmonoside, steviol monoglucosyl ester, rubusoside, steviolbioside, stevioside, rebaudioside A, rebaudioside B, rebaudioside C, rebaudioside D, rebaudioside E, rebaudioside F, rebaudioside M, dulcoside A, steviol glycoside B, steviol glycoside C, and steviol glycoside D.

[12]

The method according to any one of [8] to [11] above, wherein the second steviol glycoside is selected from the group consisting of steviolmonoside, steviolbioside, rebaudioside B, steviol glycoside A, steviol glycoside B, steviol glycoside C, and steviol glycoside D.

[13]

The method according to any one of [8] to [12] above, wherein the reaction with the first steviol glycoside is performed in the presence of an organic solvent.

[14]

The method according to [13] above, wherein the organic solvent is acetonitrile.

[15]

The method according to any one of [8] to [14] above, wherein the first steviol glycoside is a steviol glycoside wherein a branched trisaccharide, disaccharide, or glucose monosaccharide is linked through glucoside bond to the 13 position, and/or a branched trisaccharide, disaccharide, or glucose monosaccharide is linked through a glucosyl ester bond to the 19 position, and the hydrolysis of the first steviol glycoside comprises any one or more steps selected from the group consisting of the following steps (1) to (5):

(1) preferentially cleaving glycoside bond (except for rhamnoside bond) within the disaccharide or the glucoside bond or glucosyl ester bond of the glucose monosaccharide over the branched trisaccharide;

(2) preferentially cleaving glucose when xylose and glucose, or rhamnose and glucose are further linked to glucose linked to aglycone;

(3) preferentially cleaving glycoside bond (except for rhamnoside bond) within the branched trisaccharide at the 19 position over glycoside bond (except for rhamnoside bond) within the branched trisaccharide at the 13 position;

(4) preferentially cleaving glycoside bond (except for rhamnoside bond) within the branched trisaccharide or disaccharide at the 19 position and the glucosyl ester bond of the glucose monosaccharide at the 19 position over glycoside bond (except for rhamnoside bond) within the disaccharide at the 13 position; and (5) preferentially cleaving the glucosyl ester bond of the glucose monosaccharide at the 19 position over the glucoside bond of the glucose monosaccharide at the 13 position.

[16]

A method of producing steviol and/or a steviol glycoside comprising culturing a non-human transformant obtained by introducing a polynucleotide selected from the group consisting of polynucleotides (a) to (e) shown below:

(a) a polynucleotide consisting of the nucleotide sequence of SEQ ID NO: 1;

(b) a polynucleotide encoding a protein consisting of the amino acid sequence of SEQ ID NO: 2;

(c) a polynucleotide encoding a protein consisting of an amino acid sequence wherein 1 to 83 amino acids have been deleted, substituted, inserted, and/or added in the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of the first steviol glycoside;

(d) a polynucleotide encoding a protein having an amino acid sequence having a sequence identity of 90% or more to the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of the first steviol glycoside; and (e) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to hydrolyze at least one of glucoside bond at the 13 position, glucosyl ester bond at the 19 position, and glycoside bond (except for rhamnoside bond) within a side chain of the first steviol glycoside.

[17]

The method according to [16] above, wherein the polynucleotide is inserted into an expression vector.

[18]

The method according to [16] or [17] above, wherein the transformant is transformed koji mold, transformed yeast, a transformed bacterium, or a transformed plant.

Advantageous Effects of Invention

According to the present invention, there is provided a novel method of producing steviol and a steviol glycoside. With the method according to the present invention, steviol can be produced.

A steviol glycoside can be produced by selecting reaction conditions. Specifically, hydrolysis reaction of a branched trisaccharide or sophorose linked to the 13 position, or a branched trisaccharide linked to the 19 position can be suppressed by selecting reaction conditions, and a steviol glycoside having these sugar chains can be produced. As used herein, the branched trisaccharide refers to a trisaccharide wherein two glucoses are further linked to one glucose linked to aglycone, steviol wherein one of the bonds is β2→1 and the other bond is β3→1.

Specifically, rebaudioside B (rebB), steviolbioside (steB), and steviolmonoside (steM) can be produced.

In the method of the present invention, rhamnoside bond is not hydrolyzed. Therefore, a glycoside having rhamnoside can also be specifically obtained by the action of the enzyme of the present invention on a steviol glycoside mixture.

BRIEF DESCRIPTION OF DRAWINGS

FIG. 3A: only the substrate. FIG. 3B: no acetonitrile added. FIG. 3C: 8% acetonitrile.

FIG. 4A: no acetonitrile added. FIG. 4B: 8% acetonitrile.

FIG. 5A: no acetonitrile added. FIG. 5B: 8% acetonitrile.

FIG. 7A: no acetonitrile added. FIG. 7B: 4% acetonitrile. FIG. 7C: 8% acetonitrile.

FIG. 8A: no acetonitrile added. FIG. 8B: 4% acetonitrile. FIG. 8C: 8% acetonitrile.

FIG. 9A: no acetonitrile added. FIG. 9B: 4% acetonitrile. FIG. 9C: 8% acetonitrile.

FIG. 10A shows the comparison between the genomic DNA sequence (AOBGL11G) (SEQ ID NO: 4) and the cDNA sequence (AOBGL11CDS) (SEQ ID NO: 3) of AOBGL11.

FIG. 11A shows the comparison among the amino acid sequences of AOBGL11p (amino acid sequence: SEQ ID NO: 2), AOBGL3p (amino acid sequence: SEQ ID NO: 5), and AOBGL1p (amino acid sequence: SEQ ID NO: 6).

FIG. 11B shows the comparison among the amino acid sequences of AOBGL11p (amino acid sequence: SEQ ID NO: 2), AOBGL3p (amino acid sequence: SEQ ID NO: 5), and AOBGL1p (amino acid sequence: SEQ ID NO: 6) (FIG. 11A continued).

FIGS. 12A - 12D show HPLC analysis of a product using a BGL11 crude enzyme solution with rebaudioside C (0.05 mg/ml) as a substrate. The reaction time was 24 hours. FIG. 12A shows data on only the substrate. FIGS. 12B, 12C, and 12D differ from each other in the concentration of the protein of the present invention (FIG. 12B: diluted 1/1000, FIG. 12C: undiluted, FIG. 12D: concentrated 20-fold).

FIGS. 13A - 13C show HPLC analysis of a product using a BGL11 crude enzyme solution with rebaudioside F (0.05 mg/ml) as a substrate. FIG. 13A shows data on only the substrate. FIGS. 13B and 13C differ from each other in reaction time (FIG. 13B: 1 hour, FIG. 13C: 24 hours).

DESCRIPTION OF EMBODIMENTS

Figure 1A:
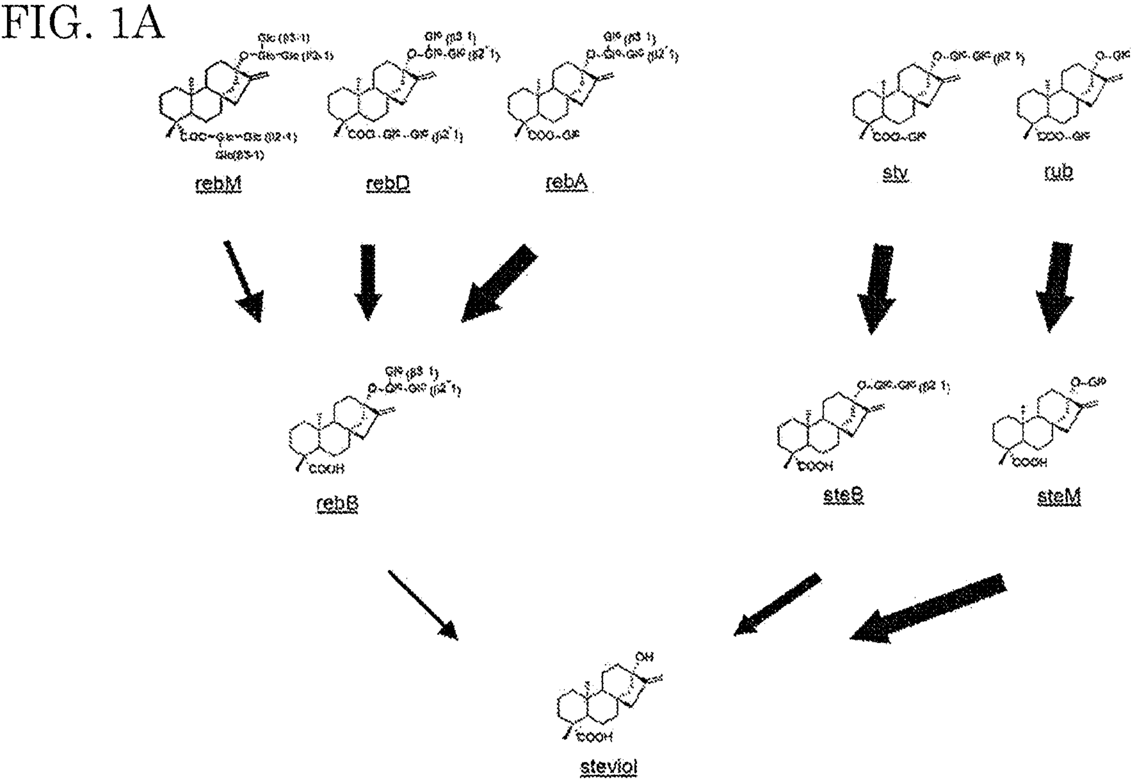
FIG. 1A shows a reaction pathway when a reaction mixture contains no organic solvent.

The present invention will be hereinafter described in detail. The following embodiments are illustrative of the present invention, and are not intended to limit the present invention. The present invention can be carried out in various manners, without departing from the gist of the invention.

Note that all documents, as well as laid-open application publications, patent application publications, and other patent documents cited herein shall be incorporated herein by reference. The present specification incorporates the contents of the specification and the drawings of Japanese Patent Application No. 2016-104404, filed on May 25, 2016, from which the present application claims priority.

"AOBGL11" designates a koji mold *Aspergillus oryzae*-derived β-glucosidase; the CDS sequence (SEQ ID NO: 1), the amino acid sequence (SEQ ID NO: 2), the ORF sequence (SEQ ID NO: 3), and the genomic DNA sequence (SEQ ID NO: 4) thereof are each shown in the accompanying Sequence Listing.

1. Method of Producing Steviol and/or a Steviol Glycoside

The present invention provides a method of producing steviol and/or a second steviol glycoside comprising reacting a protein selected from the group consisting of proteins (a) to (c) shown below (hereinafter referred to as "the protein of the present invention" with a first steviol glycoside having at least one of glucoside bond at the 13 position, glucosyl ester bond at the 19 position, and glycoside bond within a side chain, thereby hydrolyzing said at least one of glucoside bond at the 13 position, glucosyl ester bond at the 19 position, and glycoside bond (except for rhamnoside bond) within a side chain of said first steviol glycoside, wherein said first and second steviol glycosides differ from each other. In one embodiment, a glucosyl ester bond at the 19 position of the steviol glycoside is preferentially cleaved over glucoside bond at the 13 position thereof. In one embodiment, the present invention provides the method of producing steviol and/or a steviol glycoside, wherein a reaction mixture contains an organic solvent. In one embodiment, the present invention provides the method of producing steviol and/or a steviol glycoside, wherein a reaction mixture contains acetonitrile.

(a) a protein consisting of the amino acid sequence of SEQ ID NO: 2;

(b) a protein consisting of an amino acid sequence wherein 1 to 83 amino acids have been deleted, substituted, inserted, and/or added in the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of the steviol glycoside; and (c) a protein having an amino acid sequence having a sequence identity 90% or more to the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of the steviol glycoside.

While the protein shown in (b) or (c) above is typically a variant of a protein consisting of the amino acid sequence of SEQ ID NO: 2, these proteins also include proteins that can be artificially obtained using site-directed mutagenesis as described in, for example, "Sambrook & Russell, Molecular Cloning: A Laboratory Manual Vol. 4, Cold Spring Harbor Laboratory Press 2012", "Ausubel, Current Protocols in Molecular Biology, John Wiley & Sons 1987-1997", "Nuc. Acids. Res., 10, 6487 (1982)", "Proc. Natl. Acad. Sci. USA, 79, 6409 (1982)", "Gene, 34, 315 (1985)", "Nuc. Acids. Res., 13, 4431 (1985)", and "Proc. Natl. Acad. Sci. USA, 82, 488 (1985)".

Examples of the "protein consisting of an amino acid sequence wherein 1 to 83 amino acids have been deleted, substituted, inserted, and/or added in the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of the steviol glycoside" include a protein consisting of an amino acid sequence wherein, for example, 1 to 83, 1 to 80, 1 to 75, 1 to 70, 1 to 65, 1 to 60, 1 to 55, 1 to 50, 1 to 49, 1 to 48, 1 to 47, 1 to 46, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (one to several), 1 to 8, 1 to 7, 1 to 6, 1 to 5, 1 to 4, 1 to 3, 1 or 2, or 1 amino acid residue has been deleted, substituted, inserted, and/or added in the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of a steviol glycoside. In general, the number of deleted, substituted, inserted, and/or added amino acid residues is preferably smaller.

Examples of such proteins include a protein having an amino acid sequence sharing a sequence identity or 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of a steviol glycoside. In general, the value of sequence identity is preferably greater.

As used herein, the phrase "activity to hydrolyze at least one of glucoside bond at the 13 position, glucosyl ester bond at the 19 position, and glycoside bond within a side chain of the steviol glycoside" refers to the activity to cleave (hydrolyze) at least one of an O-glucoside bond at the 13 position, glucosyl ester bond at the 19 position, and glycoside bond (except for rhamnoside bond) within a side chain of steviol in a steviol glycoside, which is a glycoside wherein sugars are linked to aglycone, steviol. In an embodiment, all glucoside bonds (except for rhamnoside bond) and glucosyl ester bonds are hydrolyzed to form steviol from the steviol glycoside. In another embodiment, the first steviol glycoside is a steviol glycoside wherein a branched trisaccharide, disaccharide, or glucose is linked to the 13 position, and a branched trisaccharide, disaccharide, or glucose is linked to the 19 position. Hydrolysis reaction of the branched trisaccharide or disaccharide linked to the 13 position, or the branched trisaccharide linked to the 19 position is suppressed in the first steviol glycoside so that glucoside bond at the 13 position or glucoside bond or glucosyl ester bond within the disaccharide at the 19 position is preferentially hydrolyzed. In a further alternative embodiment, a glucosyl ester bond at the 19 position of the steviol glycoside is preferentially cleaved over glucoside bond at the 13 position thereof. As stated above, a portion of hydrolysis reaction is suppressed, thereby forming a steviol glycoside wherein only some sugars have been cleaved.

As used herein, the glycoside bond refers to a covalent bond that is formed through the dehydrative condensation between a sugar and sugar or between a sugar and another organic compound. Among glycoside bonds, a bond with carbon at the 1 position of glucose is referred to as glucoside bond, a bond with carbon at the 1 position of rhamnose is referred to as rhamnoside bond, and a bond with carbon at the 1 position of xylose is referred to as a xyloside bond.

The protein of the present invention cleaves the bond between steviol (aglycone) and a sugar (glucoside bond at the 13 position and glucosyl ester bond at the 19 position), and glycoside bond within a side chain of the steviol glycoside. The bond to be thus cleaved excludes rhamnoside bond.

In an embodiment, the first steviol glycoside is a steviol glycoside wherein a branched trisaccharide, disaccharide, or glucose monosaccharide is linked through glucoside bond to the 13 position, and/or a branched trisaccharide, disaccharide, or glucose monosaccharide is linked through a glucosyl ester bond to the 19 position, and in the present invention, any one or more cleavages selected from the group consisting of the following cleavages (1) to (5) can be performed:

(1) preferential cleavage of glycoside bond (except for rhamnoside bond) within the disaccharide or the glucoside bond or glucosyl ester bond of the glucose monosaccharide over the branched trisaccharide;

(2) preferential cleavage of glucose when xylose and glucose, or rhamnose and glucose are further linked to glucose linked to aglycone;

(3) preferential cleavage of glycoside bond (except for rhamnoside bond) within the branched trisaccharide at the 19 position over glycoside bond (except for rhamnoside bond) within the branched trisaccharide at the 13 position;

(4) preferential cleavage of glycoside bond (except for rhamnoside bond) within the branched trisaccharide or disaccharide at the 19 position and the glucosyl ester bond of the glucose monosaccharide at the 19 position over glycoside bond (except for rhamnoside bond) within the disaccharide at the 13 position; and (5) preferential cleavage of the glucosyl ester bond of the glucose monosaccharide at the 19 position over the glucoside bond of the glucose monosaccharide at the 13 position.

The activity to hydrolyze at least one of glucoside bond at the 13 position, glucosyl ester bond at the 19 position, and glycoside bond (except for rhamnoside bond) within a side chain of the steviol glycoside can be confirmed by reacting the protein of the present invention with a steviol glycoside such as steviolmonoside, steviol monoglucosyl ester, rubusoside, steviolbioside, stevioside, rebaudioside B, rebaudioside A, rebaudioside C, rebaudioside D, rebaudioside E, rebaudioside F, or rebaudioside M, purifying the resulting reaction product, and analyzing the purified product using a known technique such as liquid chromatography (LC).

The phrase "an amino acid sequence wherein 1 to 83 amino acid residues have been deleted, substituted, inserted, and/or added in the amino acid sequence of SEQ ID NO: 2" means that 1 to 83 amino acid residues have been deleted, substituted, inserted, and/or added at any 1 to 83 positions in the same sequence, wherein two or more of deletion, substitution, insertion, and addition may occur simultaneously.

Examples of amino acid residues that are interchangeable are shown below. The amino acid residues included in the same group are interchangeable.

Group A: leucine, isoleucine, norleucine, valine, norvaline, alanine, 2-aminobutanoic acid, methionine, o-methylserine, t-butylglycine, t-butylalanine, and cyclohexylalanine;

Group B: aspartic acid, glutamic acid, isoaspartic acid, isoglutamic acid, 2-aminoadipic acid, and 2-aminosuberic acid;

Group C: asparagine and glutamine;

Group D: lysine, arginine, ornithine, 2,4-diaminobutanoic acid, and 2,3-diaminopropionic acid;

Group E: proline, 3-hydroxyproline, and 4-hydroxyproline;

Group F: serine, threonine, and homoserine; and

Group G: phenylalanine and tyrosine.

The protein of the present invention can be obtained by, for example, expressing a polynucleotide encoding this protein (see "the polynucleotide of the present invention" described below) in appropriate host cells, although it can also be produced by a chemical synthesis method such as the Fmoc method (fluorenylmethyloxycarbonyl method) or the tBoc method (t-butyloxycarbonyl method). The protein of the present invention can also be chemically synthesized using a peptide synthesizer from AAPPTec LLC, Perkin Elmer Inc., Protein Technologies Inc., PerSeptive Biosystems, Applied Biosystems, or SHIMADZU CORPORATION, for example.

As used herein, the term "steviol glycoside" refers to glycoside wherein sugars are linked to aglycone, steviol. Examples of steviol and steviol glycosides are represented by the following formula (I).

[Formula 1]

(I)

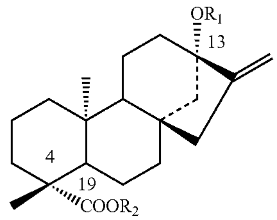

TABLE 1

| Steviol Glycoside | | |
|---|---|---|
| Compound Name | $R_1$ | $R_2$ |
| Steviol (steviol) | H | H |
| Steviolmonoside (steM) | Glcβ1- | H |
| Steviol monoglucosyl ester (steE) | H | Glcβ1- |
| Steviolbioside (steB) | Glcβ1,2Glcβ1- | H |
| Rubusoside (rub) | Glcβ1- | Glcβ1- |
| Steviol glycoside A | Rhaα1,2Glcβ1- | H |
| Steviol glycoside B | Xylβ1,2Glcβ1- | H |
| Steviol glycoside C | Rhaα1,2(Gluβ1,3)Glcβ1- | H |
| Steviol glycoside D | Xylβ1,2(Gluβ1,3)Glcβ1- | H |
| Dulcoside A (DulA) | Rhaα1,2Glcβ1- | Glcβ1- |
| Stevioside (stv) | Glcβ1,2Gluβ1- | Glcβ1- |
| Rebaudioside A (rebA) | Glcβ1,2(Gluβ1,3)Gluβ1- | Glcβ1- |
| Rebaudioside B (rebB) | Glcβ1,2(Gluβ1,3)Gluβ1- | H |
| Rebaudioside C (rebC) | Rhaα1,2(Gluβ1,3)Gluβ1- | Glc- |
| Rebaudioside D (rebD) | Glcβ1,2(Gluβ1,3)Gluβ1- | Glcβ1,2Glcβ1- |
| Rebaudioside E (rebE) | Glcβ1,2Gluβ1- | Glcβ1,2Gluβ1- |
| Rebaudioside F (rebF) | Xylβ1,2(Gluβ1,3)Glcβ1- | Glcβ1- |
| Rebaudioside M (rebM) | Glcβ1,2(Gluβ1,3)Gluβ1- | Glcβ1,2(Gluβ1,3)Gluβ1- |

In the table shown above, the steviol glycosides A and C are products obtained by reacting rebaudioside C with the protein of the present invention, and the steviol glycosides B and D are products obtained by reacting rebaudioside F with the protein of the present invention. Compounds corresponding to steviol glycosides A to D have no nominal name and are therefore referred to as "steviol glycosides A to D" as temporal designations in the present application.

In the table shown above, "Glc" designates glucose and "Glc-" designates the inclusion of a monoglucoside bond ($R_1$ position) or monoglucosyl ester bond ($R_2$ position).

"Rha" and "Xyl" designate rhamnose and xylose, respectively. When the sugar chain linked to the $R_1$ position or $R_2$ position is a branched trisaccharide, this represents that two glucoses are further linked to one glucose linked to aglycone, steviol wherein one of the bonds is a β1,2 bond and the other bond is a β1,3 bond in a branched manner. The phrase "side chain" refers to a sugar or sugar chain linked to steviol.

Figure 1B:
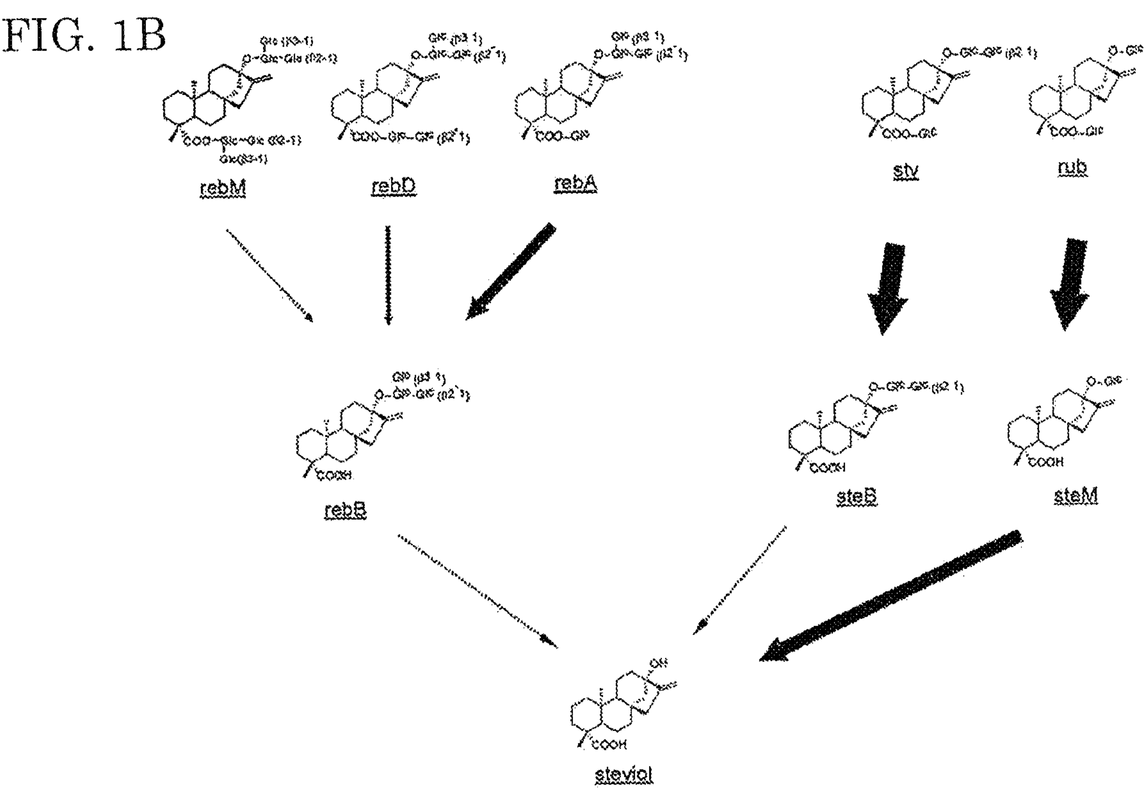
FIG. 1B shows a reaction pathway when a reaction mixture contains acetonitrile.

The method of producing a steviol glycoside and/or steviol according to the present invention hydrolyzes at least one of glucoside bond at the 13 position, glucosyl ester bond at the 19 position, and glycoside bond (except for rhamnoside bond) within a side chain of the steviol glycoside. Examples thereof are shown in a drawing (FIG. 1). Table 2 summarizes substrates and products when a reaction mixture contains no organic solvent. Table 3 summarizes substrates and products when a reaction mixture is supplemented with acetonitrile.

TABLE 2

| Substrate | Product |
|---|---|
| Rubusoside | Steviolmonoside, Steviol |
| Stevioside | Steviolbioside, Steviol |
| Rebaudioside A | Rebaudioside B, Steviol |
| Rebaudioside D | Rebaudioside B, Steviol |
| Rebaudioside M | Rebaudioside B, Steviol |

TABLE 3

| Substrate | Product |
|---|---|
| Rubusoside | Steviolmonoside, Steviol |
| Stevioside | Steviolbioside |
| Rebaudioside A | Rebaudioside B |
| Rebaudioside D | Rebaudioside B |
| Rebaudioside M | Not detected |

In the case of using the enzyme of the present invention, all glycoside bonds (except for rhamnoside bond) and glucosyl ester bonds of the steviol glycoside are hydrolyzed to form steviol, when a reaction mixture contains no organic solvent.

As for the activity of the enzyme of the present invention, hydrolyzing activity against some glycoside bonds or glucosyl ester bonds can be suppressed by a method such as addition of a solvent such as acetonitrile into a reaction mixture. That is, hydrolysis reaction of glycoside bond within a side chain of the branched trisaccharide or disaccharide linked to the 13 position, or glycoside bond of the branched trisaccharide linked to the 19 position is suppressed by the addition of an organic solvent such as acetonitrile into a reaction mixture so that glucoside bond at the 13 position, glycoside bond within the disaccharide at the 19 position, or a glucosyl ester bond at the 19 position of the steviol glycoside is preferentially cleaved. This can yield, for example, rebaudioside B from rebaudioside D or rebaudioside A, or steviolbioside from stevioside. For example, steviol glycosides other than rebaudioside M, rebaudioside B, and steviolbioside in a steviol glycoside mixture may be hydrolyzed into steviol, thereby facilitating the purification of these steviol glycosides.

In the present application, the phrase "a glucosyl ester bond at the 19 position of the steviol glycoside is preferentially cleaved over glucoside bond at the 13 position thereof" refers to the selective hydrolysis of the glucosyl ester bond at the 19 position of the steviol glycoside in preference to the glucoside bond at the 13 position thereof. For example, when rubusoside or stevioside is used as a substrate, steviolmonoside or steviolbioside is preferentially produced over steviol or steviol monoglucosyl ester. When rebaudioside D or rebaudioside A is used as a substrate, rebaudioside B is preferentially produced over steviol.

In the present application, the phrase "preferentially cleaving glycoside bond (except for rhamnoside bond) within the disaccharide or the glucoside bond or glucosyl ester bond of the glucose monosaccharide over the branched trisaccharide" refers to the preferential hydrolysis of a bond within the disaccharide of a substrate or a bond of the glucose monosaccharide with aglycone when the substrate is linked at its 13 position or 19 position to the branched trisaccharide and when the substrate is linked to the disaccharide or the glucose monosaccharide. For example, when a steviol glycoside mixture is used as a substrate, few branched trisaccharides at side chains of rebaudioside M, rebaudioside D, rebaudioside A, and rebaudioside B are hydrolyzed whereas glucoside bond of the disaccharide within a side chain at the 19 position, or glucoside bond of the disaccharide within a side chain at the 19 position or a glucosyl ester bond at the 19 position in the steviol glycoside having the glucosyl ester bond at the 19 position is hydrolyzed by preference.

The phrase "preferentially cleaving glucose when xylose and glucose, or rhamnose and glucose are further linked to glucose linked to aglycone" refers to the preferential hydrolysis of a β1,3 bond with glucose, for example, when the enzyme of the present invention is contacted with a steviol glycoside wherein xylose (β1,2 bond) and glucose (β1,3 bond) are further linked to glucose linked to the 13 position of steviol. The hydrolysis of rebaudioside F by this step preferentially hydrolyzes a glycosyl ester at the 19 position and subsequently hydrolyzes a glucose (β1,3) bond of the branched trisaccharide at the 13 position.

In "preferentially cleaving glycoside bond (except for rhamnoside bond) within the branched trisaccharide at the 19 position over glycoside bond (except for rhamnoside bond) within the branched trisaccharide at the 13 position", the contact of rebaudioside M with the enzyme of the present invention, for example, yields rebaudioside B as an intermediate product and yields steviol as a final degradation product.

In "preferentially cleaving glycoside bond (except for rhamnoside bond) within the branched trisaccharide or disaccharide at the 19 position and the glucosyl ester bond of the glucose monosaccharide at the 19 position over glycoside bond (except for rhamnoside bond) within the disaccharide at the 13 position", for example, the hydrolysis of rebaudioside M under conditions that suppress hydrolysis reaction by the addition of an organic solvent such as acetonitrile into a reaction mixture hydrolyzes the branched trisaccharide at the 19 position to form rebaudioside B. In this respect, the branched trisaccharide at the 19 position is preferentially hydrolyzed over the branched trisaccharide at the 13 position. As another example, when stevioside is hydrolyzed, the glucosyl ester bond of the glucose monosaccharide at the 19 position is preferentially cleaved compared to the hydrolysis of the disaccharide at the 13 position to form steviolbioside.

In "preferentially cleaving the glucosyl ester bond of the glucose monosaccharide at the 19 position over the glucoside bond of the glucose monosaccharide at the 13 position", for example, the hydrolysis of rubusoside by the enzyme of the present invention preferentially cleaves the glucosyl ester bond of the glucose monosaccharide at the 19 position to form steviolmonoside as an intermediate.

In the method of producing a steviol glycoside and/or steviol according to the present invention, the steviol glycoside having at least one of glucoside bond at the 13 position, glucosyl ester bond at the 19 position, and glycoside bond within a side chain for use as the starting material can be obtained by extraction from *Stevia rebaudiana* or *Rubus suavissimus* followed by purification using known methods including extraction with an appropriate solvent (an aqueous solvent such as water, or an organic solvent such as an alcohol, ether, or acetone), a gradient between water and ethyl acetate or other organic solvent, high performance liquid chromatography (HPLC), and ultra (high) performance liquid chromatography (UPLC). Alternatively, a commercially-available product may be used as the steviol glycoside having at least one of glucoside bond at the 13 position, glucosyl ester bond at the 19 position, and glycoside bond within a side chain for use as the starting material.

The method of producing a steviol glycoside and/or steviol according to the present invention comprises reacting the protein of the present invention with a steviol glycoside having at least one of glucoside bond at the 13 position, glucosyl ester bond at the 19 position, and glycoside bond within a side chain, thereby hydrolyzing said at least one of glucoside bond at the 13 position, glucosyl ester bond at the 19 position, and glycoside bond (except for rhamnoside bond) within a side chain. The method of the present invention may further comprise purifying the steviol and/or second steviol glycoside of the present invention which is produced in the above step.

Steviol and/or the steviol glycoside according to the present invention which has no monoglucoside bond or glucosyl ester bond can be purified using known methods including extraction with an appropriate solvent (an aqueous solvent such as water, or an organic solvent such as an alcohol, ether, or acetone), a gradient between water and ethyl acetate or other organic solvent, high performance liquid chromatography (HPLC), and ultra (high) performance liquid chromatography (UPLC).

The method of producing a steviol glycoside and/or steviol according to the present invention can be performed under conditions where a reaction mixture containing a substrate is supplemented with an organic solvent. The amount of the organic solvent can be in the range of 1% to 20% with respect to the total amount of the reaction mixture and is preferably 5% to 15% or 6 to 12%, more preferably 8%. The organic solvent can be a generally available organic solvent and is preferably an organic solvent for use as a mixture with water at any ratio. Acetonitrile can be used. The organic solvent may be added to a reaction mixture in advance or may be added during the course of the reaction.

As used herein, the term "polynucleotide" refers to DNA or RNA.

Examples of the polynucleotide encoding the protein consisting of the amino acid sequence of SEQ ID NO: 2 include a polynucleotide consisting of the nucleotide sequence of SEQ ID NO: 1.

Examples of the "protein consisting of an amino acid sequence wherein 1 to 83 amino acids have been deleted, substituted, inserted, and/or added in the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of a steviol glycoside" are as described above.

Examples of the "protein having an amino acid sequence having a sequence identity of 90% or more to the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of a steviol glycoside" are as described above.

As used herein, the phrase "a polynucleotide which hybridizes under highly stringent conditions" refers to a polynucleotide obtained by means of a hybridization method such as colony hybridization, plaque hybridization, or Southern hybridization, using, as a probe, all of or a portion of a polynucleotide consisting of a nucleotide sequence complementary to the nucleotide sequence of SEQ ID NO: 1 or a polynucleotide consisting of a nucleotide sequence complementary to a nucleotide sequence encoding the amino acid sequence of SEQ ID NO: 2. For hybridization, methods as described in "Sambrook & Russell, Molecular Cloning: A Laboratory Manual Vol. 4, Cold Spring Harbor, Laboratory Press 2012" and "Ausubel, Current Protocols in Molecular Biology, John Wiley & Sons 1987-1997", for example, can be used.

As used herein, the term "highly stringent conditions" refers to, for example, the following conditions: 5×SSC, 5×Denhardt's solution, 0.5% SDS, 50% formamide, 50° C.; 0.2×SSC, 0.1% SDS, 60° C.; 0.2×SSC, 0.1% SDS, 62° C.; or 0.2×SSC, 0.1% SDS, 65° C.; although not limited thereto. Under these conditions, it is expected that DNA having a higher sequence identity will be efficiently obtained at a higher temperature. Note, however, that a plurality of factors such as temperature, probe concentration, probe length, ionic strength, time, and salt concentration are considered to affect the stringency of hybridization, and a person skilled in the art will be able to achieve the same stringency by selecting these factors as appropriate.

When a commercially available kit is used for hybridization, the Alkphos Direct Labelling and Detection System (GE Healthcare), for example, can be used. In this case, hybridization is accomplished in accordance with the protocol attached to the kit, i.e., a membrane may be incubated overnight with a labeled probe and then washed with a primary washing buffer containing 0.1% (w/v) SDS at 55 to 60° C. to detect the hybridized DNA. Alternatively, when a commercially available reagent (e.g., PCR labeling mix (Roche Diagnostics)) is used for digoxigenin (DIG) labeling of a probe during probe preparation based on all of or a portion of a nucleotide sequence complementary to the nucleotide sequence of SEQ ID NO: 1 or a nucleotide sequence complementary to a nucleotide sequence encoding the amino acid sequence of SEQ ID NO: 2, the DIG nucleic acid detection kit (Roche Diagnostics) may be used for detection of hybridization.

In addition to those described above, examples of other hybridizable polynucleotides include DNA sharing 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more sequence identity with DNA of the nucleotide sequence of SEQ ID NO: 1 or DNA encoding the amino acid sequence of SEQ ID NO: 2, as calculated by the homology search software BLAST using default parameters.

Note that the sequence identity of amino acid sequences or nucleotide sequences can be determined using the BLAST algorithm developed by Karlin and Altschul (Basic Local Alignment Search Tool) (Proc. Natl. Acad. Sci. USA 872264-2268, 1990; Proc Natl Acad Sci USA 90: 5873, 1993). When BLAST is used, default parameters in each program are used.

The above-described polynucleotide of the present invention can be obtained using a known genetic engineering technique or a known synthesis technique.

The polynucleotide of the present invention may further contain a polynucleotide consisting of a nucleotide sequence encoding a secretory signal peptide. Preferably, the polynucleotide of the present invention contains, at its 5' end, the polynucleotide consisting of a nucleotide sequence encoding a secretory signal peptide. The secretory signal peptide and the polynucleotide consisting of a nucleotide sequence encoding the secretory signal peptide are the same as described above.

The polynucleotide of the present invention is preferably inserted into an appropriate expression vector for introduction into a host.

An appropriate expression vector is typically configured to include:

(i) a promoter transcribable in host cells;

(ii) the polynucleotide of the present invention ligated to the promoter; and (iii) an expression cassette containing, as constituent elements, signals that function in the host cells for transcription termination and polyadenylation of an RNA molecule.

Examples of methods for preparing such an expression vector include, although not particularly limited to, using plasmids, phages, cosmids, or the like.

The specific type of the vector is not particularly limited, and any vector expressible in host cells may be selected as appropriate. Specifically, an appropriate promoter sequence may be selected in accordance with the type of the host cells to ensure the expression of the polynucleotide of the present invention, and this promoter sequence and the polynucleotide of the present invention may then be integrated into any of various plasmids, for example, for use as an expression vector.

The expression vector of the present invention contains an expression control region (e.g., a promoter, a terminator, and/or a replication origin), depending on the type of the host into which the expression vector is to be introduced. For bacterial expression vectors, commonly used promoters (e.g., trc promoter, tac promoter, and lac promoter) are used. Examples of yeast promoters include glyceraldehyde-3-phosphate dehydrogenase promoter and PH05 promoter. Examples of filamentous fungi promoters include amylase and trpC. Moreover, examples of promoters for expression of a target gene in plant cells include cauliflower mosaic virus 35S RNA promoter, rd29A gene promoter, rbcS promoter, and mac-1 promoter configured to have the enhancer sequence of the above-mentioned cauliflower mosaic virus 35S RNA promoter at the 5'-side of *Agrobacterium*-derived mannopine synthase promoter sequence. Examples of promoters for animal cell hosts include viral promoters (e.g., SV40 early promoter and SV40 late promoter). Examples of promoters inducibly activated by external stimulation include mouse mammary tumor virus (MMTV) promoter, tetracycline-responsive promoter, metallothionein promoter, and heat-shock protein promoter.

The expression vector preferably contains at least one selection marker. For use as such a marker, auxotrophic markers (ura5, niaD), drug resistance markers (hygromycin, zeocin), geneticin resistance gene (G418r), copper resistance gene (CUP1) (Marin et al., Proc. Natl. Acad. Sci. USA, vol. 81, p. 337, 1984), cerulenin resistance genes (fas2m, PDR4) (Junji Inokoshi et al., Biochemistry, vol. 64, p. 660, 1992; Hussain et al., Gene, vol. 101, p. 149, 1991), and the like are available.

While the method of preparing (producing) the transformant of the present invention is not particularly limited, the transformant of the present invention may be prepared by, for example, introducing an expression vector containing the polynucleotide of the present invention into a host to transform the host. Any of conventionally known various types of cells or organisms can be suitably used as the cells or organism to be transformed. Examples of the cells to be transformed include bacteria such as *Escherichia coli*, yeast (budding yeast *Saccharomyces cerevisiae*, fission yeast *Schizosaccharomyces pombe*), filamentous fungi (koji mold *Aspergillus oryzae, Aspergillus sojae*), plant cells, and non-human animal cells. Appropriate media and conditions for culturing the above-described host cells are well known in the art. Likewise, the organism to be transformed is not particularly limited, and examples include various microorganisms, plants, and non-human animals described above as examples of host cells. The transformant is preferably yeast or a plant.

The host to be used in transformation preferably produces a steviol glycoside having at least one of glucoside bond at the 13 position, glucosyl ester bond at the 19 position, and glycoside bond within a side chain. The host that can be used may include not only a plant such as *Stevia rebaudiana* or *Rubus suavissimus* that originally produces a steviol glycoside having at least one glucoside bond at the 13 position, glucosyl ester bond at the 19 position, and/or glycoside bond within a side chain, but also a host in which a gene required for the production of a steviol glycoside having at least one glucoside bond at the 13 position, glucosyl ester bond at the 19 position, and/or glycoside bond within a side chain into cells or an organism that does not originally produce a steviol glycoside having glucoside bond at the 13 position, glucosyl ester bond at the 19 position, and/or glycoside bond within a side chain, is introduced. Examples of the "gene required for the production of a steviol glycoside having at least one of glucoside bond at the 13 position, glucosyl ester bond at the 19 position, and glycoside bond within a side chain" include genes having steviol or steviol glycoside synthesis activity such as those described in WO 2011093509.

For transformation of the host cells, commonly used known methods can be used. For example, transformation can be accomplished using electroporation (Mackenxie, D. A. et al., Appl. Environ. Microbiol., vol. 66, p. 4655-4661, 2000), the particle delivery method (described in JP 2005-287403 A entitled "Breeding Method of Lipid Producing Fungi"), the spheroplast method (Proc. Natl. Acad. Sci. USA, vol. 75, p. 1929, 1978), the lithium acetate method (J. Bacteriology, vol. 153, p. 163, 1983), and other methods as described in Methods in yeast genetics, 2000 Edition: A Cold Spring Harbor Laboratory Course Manual, although not limited thereto. When a gene is introduced into a plant or into tissues or cells from a plant, a method selected from the *Agrobacterium* method (Plant Molecular Biology Manual, Gelvin, S. B. et al., Academic Press Publishers), particle gun method, PEG method, electroporation, etc. can be used as appropriate.

When the transformant is yeast or koji mold, the yeast or koji mold transformed with the polynucleotide of the present invention expresses a higher level of the protein of the present invention than in the wild-type counterpart. Thus, the expressed protein of the present invention reacts with the first steviol glycoside having at least one of glucoside bond at the 13 position, glucosyl ester bond at the 19 position, and glycoside bond within a side chain produced in the yeast or koji mold, thereby cleaving said at least one of glucoside bond at the 13 position, glucosyl ester bond at the 19 position, and glycoside bond (except for rhamnoside bond) within a side chain of said first steviol glycoside. As a result, the steviol and/or second steviol glycoside is produced in the cells or culture medium of the yeast or koji mold, preferably in the culture medium.

When the transformant is a plant, the plant to be transformed in the present invention refers to any of whole plants, plant organs (e.g., leaves, petals, stems, roots, and seeds), plant tissues (e.g., epidermis, phloem, parenchyma, xylem, vascular bundles, palisade tissue, and spongy parenchyma) or plant cultured cells, or various forms of plant cells (e.g., suspension cultured cells), protoplasts, leaf sections, calli, and the like. The plant used for transformation may be a plant in the class of either monocotyledons or dicotyledons. The introduction of the polynucleotide of the present invention into the plant can be confirmed by using PCR, Southern hybridization, or Northern hybridization, for example. Once a transformed plant in which the polynucleotide of the present invention has been integrated into the genome is obtained, progeny plants can be produced by sexual or asexual reproduction of the plant. Moreover, seeds, fruits, cuttings, tubers, root tubers, rootstocks, calli, protoplasts or the like can be obtained from this plant or progeny plants thereof, or clones thereof, and used to achieve mass production of the plant. The plant transformed with the polynucleotide of the present invention (hereinafter, "the plant of the present invention") contains a greater amount of the protein of the present invention than in the wild-type counterpart. Thus, the protein of the present invention reacts with the steviol glycoside having at least one of glucoside bond at the 13 position, glucosyl ester bond at the 19 position, and glycoside bond within a side chain produced in the plant of the present invention. As a result, the steviol is produced in the plant. When the internal environment of the plant is not optimal for hydrolysis reaction, hydrolysis reaction of the branched trisaccharide or disaccharide linked to the 13 position, or the branched trisaccharide linked to the 19 position is suppressed. As a result, a steviol glycoside wherein a monoglucoside bond at the 13 position, glycoside bond within the disaccharide linked to the 19 position, or a glucosyl ester bond at the 19 position has been cleaved is produced.

In an embodiment, the transformant of the present invention or the culture medium thereof has a content of the Steviol glycoside of the present invention higher than that in the wild-type counterpart, and an extract or the culture medium of the transformant contains a high concentration of the Steviol glycoside of the present invention. An extract of the transformant of the present invention can be obtained by homogenating the transformant with glass beads, a homogenizer, or a sonicator, for example, centrifuging the homogenate, and collecting the supernatant. When the Steviol glycoside of the present invention accumulates in the culture medium, the transformant and the culture supernatant may be separated using a standard method (e.g., centrifugation or filtration) after the completion of culture, thereby obtaining the culture supernatant containing the Steviol glycoside of the present invention.

The extract or culture supernatant thus obtained may be further subjected to a purification step. The Steviol glycoside of the present invention may be purified in accordance with a standard separation and purification method. Specific methods for purification are the same as described above.

Method of Producing the Steviol Glycoside and/or Steviol of the Present Invention Using an Enzyme from Non-Human Transformed Cells The protein of the present invention can be obtained by expressing the protein of the present invention in host cells and homogenating the cells. The steviol glycoside and/or steviol of the present invention can also be produced by the action of the protein of the present invention.

Specifically, the steviol can be produced by contacting an enzyme from the transformed cells of the present invention with a steviol glycoside having at least one of glucoside bond at the 13 position, glucosyl ester bond at the 19 position, and glycoside bond within a side chain. Hydrolysis reaction of the branched trisaccharide or disaccharide linked to the 13 position, or the branched trisaccharide linked to the 19 position is suppressed by the addition of an organic solvent such as acetonitrile into a reaction mixture. As a result, a steviol glycoside wherein a monoglucoside bond at the 13 position, glycoside bond within the disaccharide linked to the 19 position, or a glucosyl ester bond at the 19 position has preferentially been cleaved is produced. The protein of the present invention has been confirmed in Examples to exhibit equivalent activity both when expressed in yeast and when expressed in koji mold.

The "enzyme from transformed cells" is not limited as long as it is prepared using transformed cells, and contains the protein of the present invention. Examples of the enzyme include transformed cells themselves, a transformed cell homogenate itself, transformed cell culture supernatant itself, and a purified product thereof. Thus, the present invention provides a method of producing steviol and/or a second steviol glycoside comprising contacting an enzyme from a non-human transformed cell obtained by introducing, into a host cell, a polynucleotide selected from the group consisting of polynucleotides (a) to (e) shown below, with a first steviol glycoside having at least one of glucoside bond at the 13 position, glucosyl ester bond at the 19 position, and glycoside bond within a side chain, thereby hydrolyzing said at least one of glucoside bond at the 13 position, glucosyl ester bond at the 19 position, and glycoside bond (except for rhamnoside bond) within a side chain of said first steviol glycoside, wherein said first and second steviol glycosides differ from each other:

(a) a polynucleotide consisting of the nucleotide sequence of SEQ ID NO: 1;

(b) a polynucleotide encoding a protein consisting of the amino acid sequence of SEQ ID NO: 2;

(c) a polynucleotide encoding a protein consisting of an amino acid sequence wherein 1 to 83 amino acids have been deleted, substituted, inserted, and/or added in the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of the steviol glycoside;

(d) a polynucleotide encoding a protein having an amino acid sequence having a sequence identity of 90% or more to the amino acid sequence of SEQ ID NO: 2, and having an activity to hydrolyze at least one of glucoside bond at the 13 position, glucosyl ester bond at the 19 position, and glycoside bond (except for rhamnoside bond) within a side chain of the steviol glycoside; and (e) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to hydrolyze at least one of glucoside bond at the 13 position, glucosyl ester bond at the 19 position, and glycoside bond (except for rhamnoside bond) within a side chain of the steviol glycoside.

The polynucleotide selected from the group consisting of polynucleotides (a) to (e) shown above is the polynucleotide of the present invention, which is the same as described above.

The term "contact" refers to causing the enzyme from the transformed cells of the present invention and the steviol glycoside having at least one of glucoside bond at the 13 position, glucosyl ester bond at the 19 position, and glycoside bond within a side chain to exist in the same reaction or culture system. The term "contact" includes, for example, adding the steviol glycoside having at least one of glucoside bond at the 13 position, glucosyl ester bond at the 19 position, and glycoside bond within a side chain to a container containing the enzyme from the transformed cells of the present invention, mixing the enzyme from the transformed cells of the present invention and the steviol glycoside having at least one of glycoside bond at the 13 position, glucosyl ester bond at the 19 position, and glycoside bond within a side chain, and adding the enzyme from the transformed cells of the present invention to a container containing the steviol glycoside having at least one of glucoside bond at the 13 position, glucosyl ester bond at the 19 position, and glycoside bond within a side chain.

The phrases "steviol glycoside", "steviol glycoside having at least one of glucoside bond at the 13 position, glucosyl ester bond at the 19 position, and glycoside bond within a side chain", and "activity to hydrolyze at least one of glucoside bond at the 13 position, glucosyl ester bond at the 19 position, and glycoside bond (except for rhamnoside bond) within a side chain of the steviol glycoside" are the same as described above.

For other standard molecular biological techniques, reference may be made to "Sambrook & Russell, Molecular Cloning: A Laboratory Manual Vol. 4, Cold Spring Harbor Laboratory Press 2012" and "Methods in Yeast Genetics, A laboratory manual (Cold Spring Harbor Laboratory Press, Cold Spring Harbor, N.Y.)", for example.

The steviol glycoside of the present invention thus obtained can be used for such purposes as the production of foods and drinks, sweeteners, flavors, pharmaceutical products, and industrial raw materials (raw materials for cosmetics, soaps, and the like), for example, in accordance with conventional methods.

In the present invention, the term "foods and drinks" refers collectively to orally edible materials in the form of solids, fluids, liquids, and mixtures thereof. Examples of the foods and drinks of the present invention include nutritional supplement foods and drinks, health foods and drinks, functional foods and drinks, foods and drinks for children, modified milk for infants, modified milk for premature infants, and foods and drinks for the elderly.

The nutritional supplement foods and drinks refer to foods and drinks fortified with a specific nutrient. The health foods and drinks refer to foods and drinks that are healthy or supposed to be good for health and include nutritional supplement foods and drinks, natural foods and drinks, diet foods and drinks, and the like. The functional foods and drinks refer to foods and drinks for supplying a nutrient responsible for body's regulatory functions and are synonymous with foods for specified health use. The foods and drinks for children refer to foods and drinks intended for children up to about 6 years of age. The foods and drinks for the elderly refer to foods and drinks treated to facilitate digestion and absorption as compared with untreated foods and drinks. The modified milk for infants refers to modified milk intended for children up to about 1 year of age. The modified milk for premature infants refers to modified milk intended for premature infants up to about 6 months of age.

In the present application, the term "at least" means that the number of a specific item may be the recited number or larger. In the present application, the term "about" means that an entity falls within the range of ±25%, ±10%, ±5%, ±3%, ±2%, or ±1% of a value following "about". For example, the phrase "about 10" refers to the range of 7.5 to 12.5.

Note that all documents, as well as laid-open application publications, patent application publications, and other patent documents cited herein shall be incorporated herein by reference.

EXAMPLES

The present invention will be more specifically described hereinafter with reference to examples, which are not intended to limit the scope of the present invention.

Search for Koji Mold β-Glucosidase Gene

The koji mold genome data (PRJNA28175) was searched for β-glucosidase homologs, and an intracellular β-glucosidase homolog, AO090701000244 (CDS sequence: SEQ ID NO: 1, estimated amino acid sequence: SEQ ID NO: 2, ORF sequence: SEQ ID NO: 3, genomic DNA sequence: SEQ ID NO: 4), is found. This homolog was cloned as AOBGL11.

Cloning of Genomic DNA of AOBGL11

In order to clone AOBGL11, the following primers were designed:

AOBGL11-F:

5'-ATGCCTCGTCTAGACGTCGAGAA-3' (SEQ ID NO: 7)

AOBGL11-R:

5'-TCACAGACCCAACCAGTAGCGA-3' (SEQ ID NO: 8)

Conidia of koji mold *Aspergillus oryzae* var. *Brunneus* (IFO30102) were inoculated to 10 ml of a liquid culture medium (containing, per liter, 20 g of glucose, 1 g of Bacto-tryptone, 5 g of yeast extract, 1 g of $NaNO_3$, 0.5 g of $K_2HPO_4$, 0.5 g of $MgSO_4$-$7H_2O$, and 0.01 g of $FeSO_4.7H_2O$) and cultured at 30° C. for 1 day. The cells were collected by filtration and ground in liquid nitrogen. Genomic DNA was then prepared using DNeasy Plant Mini Kit (QIAGEN).

Using the genomic DNA as a template, PCR was performed with the primers AOBGL11-F and AOBGL11-R, using KOD-Plus (Toyobo). About 2.57 kbp of the resulting DNA fragment was cloned using the Zero Blunt TOPO PCR cloning Kit (Invitrogen), thus obtaining a plasmid pCR-AOBGL11g.

Construction of Koji Mold Expression Vector

A DNA fragment obtained by digesting a koji mold vector pUNA (National Research Institute of Brewing) with a restriction enzyme SmaI, and approximately 2.57 kbp of a DNA fragment obtained by digesting the plasmid pCR-AOBGL 11g with restriction enzymes EcoRI and blunt-ending the end using Blunting Kit (Takara Bio), were ligated to obtain a plasmid pUNA-AOBGL 11g.

Transformation of Koji Mold

Koji mold was transformed as follows.

*Aspergillus oryzae* niaD300 strain (National Research Institute of Brewing) was used as a host. The host strain was inoculated to a PDA plate and cultured at 30° C. for about 1 week. In order to obtain a conidial suspension, conidia were suspended by adding 0.1% tween 80 and 0.8% NaCl. The suspension was filtered through Miracloth and then centrifuged to collect the conidia. The conidia were then washed with 0.1% tween 80 and 0.8% NaCl and suspended in sterilized water.

The conidia were applied to a CD plate (containing, per liter, 6 g of $NaNO_3$, 0.52 g of KCl, 1.52 g of $KH_2PO_4$, 10 g of glucose, 2 ml of IM $MgSO_4$, 1 ml of a trace element solution (containing, per liter, 1 g of $FeSO_4.7H_2O$, 8.8 g of $ZnSO_4.7H_2O$, 0.4 g of $CuSO_4$-$5H_2O$, 0.1 g of $NaB_4O_7.10H_2O$, and 0.05 g of $(NH_4)$ $Mo_7O_{24}.4H_2O$), and 20 g of agar (pH 6.5)), and DNA was introduced into the conidia by the particle delivery method. This was performed using PDS-1000/He (Bio-Rad), tungsten M-10 particles, and a 1100 psi rupture disc at a distance of 3 cm. A strain that grew on a CD plate was selected as the transformed strain. The strain transformed with the plasmid pUNA-AOBGL11g was designated as BGL11-1 strain, and the strain transformed with the control vector pUNA was designated as C-1 strain.

Production of AOBGL11p Using Koji Mold

BGL11-1 stain or C-1 strain was inoculated to a CD plate and cultured at 30° C. for 7 days to form conidia. In order to obtain a conidial suspension, the conidia were suspended by adding 0.1% tween 80 and 0.8% NaCl. The suspension was filtered through Miracloth and then centrifuged to collect the conidia. The conidia were then washed with 0.1% tween 80 and 0.8% NaCl and suspended in sterilized water to prepare a conidial suspension and this conidia suspension was inoculated to a liquid culture medium for enzyme production (containing, per liter, 100 g of maltose, 1 g of Bacto-tryptone, 5 g of yeast extract, 1 g of $NaNO_2$, 0.5 g of $K_2HPO_4$, 0.5 g of $MgSO_4.7H_2O$, and 0.01 g of $FeSO_4.7H_2O$) and cultured with shaking at 30° C. for 2 days. The medium was filtered through Miracloth to collect the cells. About 4 g of the resulting wet cells was frozen in liquid nitrogen and ground in a mortar. The ground cells were suspended in 50 mM sodium phosphate buffer (pH 7.0), well mixed, and then centrifuged. The resulting supernatant was concentrated by ultrafiltration through Amicon Ultra-15 50k (Merck), and the buffer was replaced with 50 mM sodium phosphate buffer (pH 7.0) containing 0.1% CHAPS (buffer A) to obtain about 1 ml of a crude enzyme solution.

Measurement of Protein Concentration

The protein concentration of the crude enzyme solution was determined using Protein Assay CBB Solution (concentrated 5-fold) (Nacalai Tesque). As a result, the protein concentration was 6.46 mg/ml for BGL11-1 crude enzyme solution and 4 mg/ml for C-1 crude enzyme solution.

pNP-β-Glc Degrading Activity pNP-β-Glc degrading activity was studied. 10 μL of the crude enzyme solution, 50 μL of a 0.2 M sodium phosphate buffer (pH 7.0), 50 μL of a 20 mM aqueous pNP-β-Glc solution, and water were mixed to a total volume of 200 μL, and the mixture was reacted at 37° C. Since BGL11-1 crude enzyme solution had high activity, the crude enzyme solution was diluted 100-fold with 50 mM sodium phosphate buffer (pH 7.0) containing 0.1% CHAPS and used. The change in absorbance at 405 nm (A405) per minute based on p-nitrophenol (pNP) liberated by the hydrolysis of pNP-β-Glc was 0.244 for BGL11-1 crude enzyme solution and 0.000 for C-1 crude enzyme solution.

These results suggested that AOBGL11p is responsible for β-glucosidase activity.

Using pNP-β-Glc as a substrate, AOBGL11p was examined for the optimum temperature, optimum pH, thermal stability, and pH stability (FIG. 2).

BGL11-1 crude enzyme solution was diluted 5000-fold with buffer A and used (protein concentration: 1.3 μg/ml).

Figure 2A:
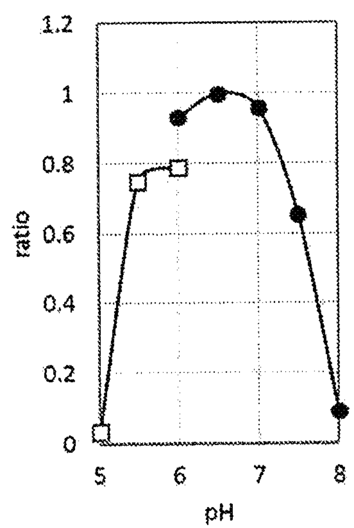
FIG. 2A shows the optimum pH of AOBGL11p with pNP-β-Glc as a substrate.
Figure 2B:
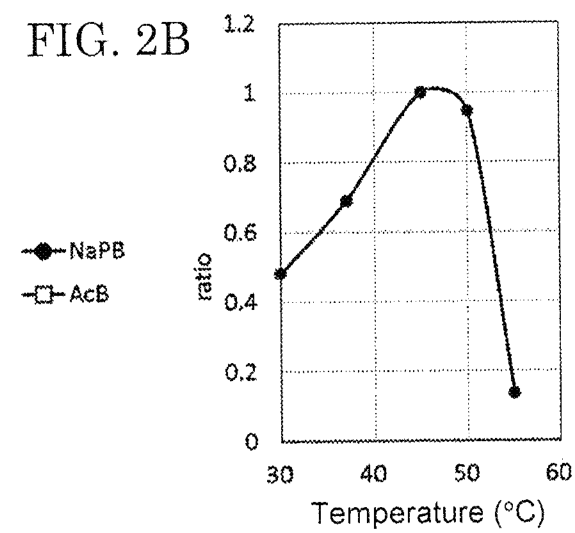
FIG. 2B shows the optimum temperature of AOBGL11p with pNP-β-Glc as a substrate.

Optimum temperature: The reaction mixture contained 20 μl of the crude enzyme solution (1.3 μg/ml), 100 μl of a 0.2 M sodium phosphate buffer (pH 6.5), 20 mM pNP-β-Glc, and water mixed to a total volume of 400 μl. 15 minutes, 30 minutes, and 45 minutes after the start of reaction, 100 μl was sampled and mixed with 100 μl of a 0.2 M sodium carbonate solution. Then, absorbance at 405 nm was measured, and Δ405 was determined. When 45° C. at which the largest value of Δ405 was obtained was defined as 1, the ratio of Δ405 from the reaction at each temperature is shown in FIG. 2B. These results indicated that 45 to 50° C. is the optimum reaction temperature.

Optimum pH: The reaction mixture contained 20 μl of the crude enzyme solution (1.3 μg/ml), 100 μl of a 0.2 M buffer, 20 mM pNP-β-Glc, and water mixed to a total volume of 400 μl. The buffer used was a sodium acetate buffer for pH 4.0 to 6.0 and a sodium phosphate buffer for pH 6.0 to 8.0. Sampling and measurement were performed in the same manner as above. The ratio of Δ405 from the reaction at each pH to the largest value of Δ405 is shown in FIG. 2A. These results indicated that pH 6.0 to 7.0 is the optimum reaction pH.

Figure 2C:
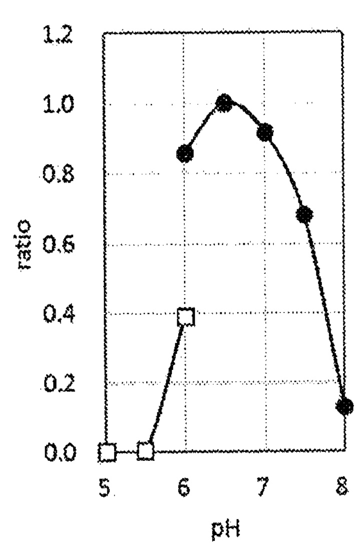
FIG. 2C shows the pH stability of AOBGL11p with pNP-β-Glc as a substrate.
Figure 2D:
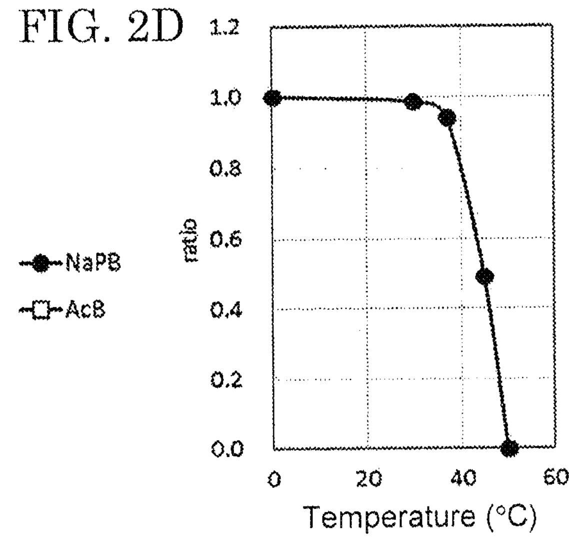
FIG. 2D shows the thermal stability of AOBGL11p with pNP-β-Glc as a substrate.

Thermal stability: The crude enzyme solution diluted 5000-fold (1.3 μg/ml) was kept at 30° C., 37° C., 45° C., and 50° C. each for 10 minutes and then cooled in ice. The reaction mixture contained 5 μl of the crude enzyme solution (1.3 μg/ml), 100 μl of a 0.2 M sodium phosphate buffer (pH 6.5), 20 mM pNP-β-Glc, and water mixed to a total volume of 100 μl, and was reacted at 37° C. for 45 minutes. Then, 100 μl of a 0.2 M sodium carbonate solution was added to the reaction mixture, and absorbance at 405 nm was measured. The ratio of absorbance at 405 nm from the treatment at each temperature to absorbance at 405 nm after 45 minutes of an enzyme solution that was not heat-treated was determined. The results are shown in FIG. 2D. AOBGL11p was found to be stable up to 37° C. in the treatment for 10 minutes, to lose about half its activity by the treatment at 45° C., and to lose almost all the activity by the treatment at 50° C.

pH stability: The crude enzyme solution was diluted 5000-fold with each buffer of pH 4.5, 5.0, 5.5, or 6.0 (0.2 M acetate buffer) or pH 6.0, 6.5, 7.0, 7.5, or 8.0 (0.2 M sodium phosphate buffer), kept at 37° C. for 1 hour, and then cooled in ice. The reaction mixture contained 5 μl of the crude enzyme solution (1.3 μg/ml), 100 μl of a 0.2 M sodium phosphate buffer (pH 6.5), 20 mM pNP-β-Glc, and water mixed to a total volume of 100 μl, and was reacted at 37° C. for 45 minutes. Then, 100 μl of a 0.2 M sodium carbonate solution was added to the reaction mixture, and absorbance at 405 nm was measured. The ratio of absorbance from the crude enzyme solution kept at each pH to absorbance from the crude enzyme solution kept at pH 6.5 that offered the highest activity was determined. The results are shown in FIG. 2C. AOBGL11p was found to be most stable around pH 6.5.

Steviol Glycoside-Hydrolyzing Activity

Rebaudioside M, rebaudioside D, rebaudioside A, stevioside, and rubusoside were used as substrates.

Steviol glycosides were analyzed by HPLC or LC-MS.

The analysis conditions for HPLC were as follows:

Column: COSMOSIL $5C_{18}$-AR-II 4.6 mm I.D.×250 mm (Nacalai Tesque)

Mobile phase: A; acetonitrile, B; 10 mM sodium phosphate buffer (pH 2.6)

B conc. 70%→30% 40 min linear gradient

Flow rate: 1 ml/min

Temperature: 40° C.

Detection: UV 210 nm

The analysis conditions for LC-MS (IT-TOF) were as follows:

Column: mtakt SM-C18 4.6×250 mm

Mobile phase: A; 0.5% acetic acid, B; methanol

B conc. 10% (0 min-5 min)→70% (20 min)→100% (25 min-30 min)→10% (31 min-40 min) Flow rate: 0.4 ml/min Reaction Conditions (1)—Reaction Mixture Contains No Organic Solvent—

50 μg/ml of a substrate, 20 μl of BGL11 crude enzyme solution (protein concentration: 6.5 mg/ml), and 50 mM sodium phosphate buffer (pH 6.5) were mixed to a total volume of 100 μl, and the mixture was reacted at 37° C. for 24 hours. The reaction mixture was passed through Sep-Pak C18 (Waters) washed with acetonitrile and equilibrated with water. The reaction product was subsequently washed with 20% acetonitrile and then eluted with 50% acetonitrile. The eluate was evaporated to dryness with SpeedVac. The resulting product was dissolved in 100 μL of water, and the solution was subjected to HPLC. When the substrate was rebM, LC-MS was also performed.

Figure 3A:
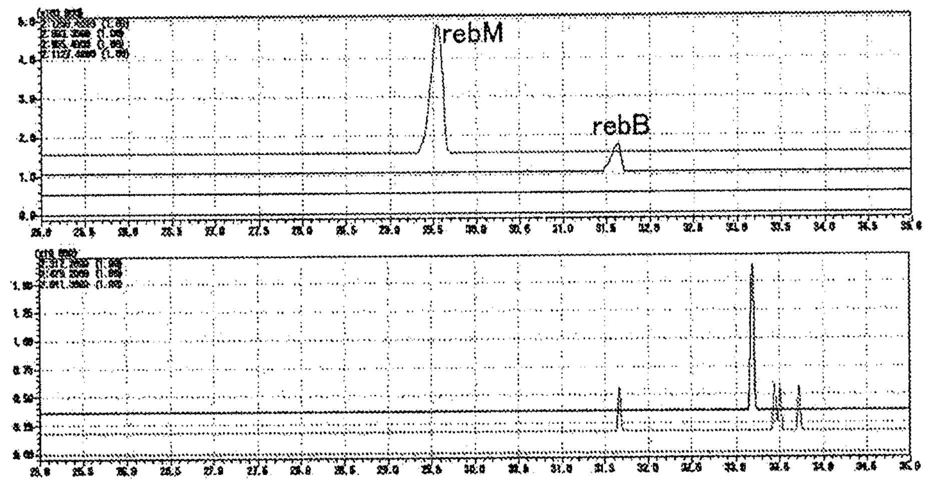
FIGS. 3A - 3C show LC-MS analysis of a product using a BGL11 crude enzyme solution with rebM (0.05 mg/ml) as a substrate.
Figure 3B:
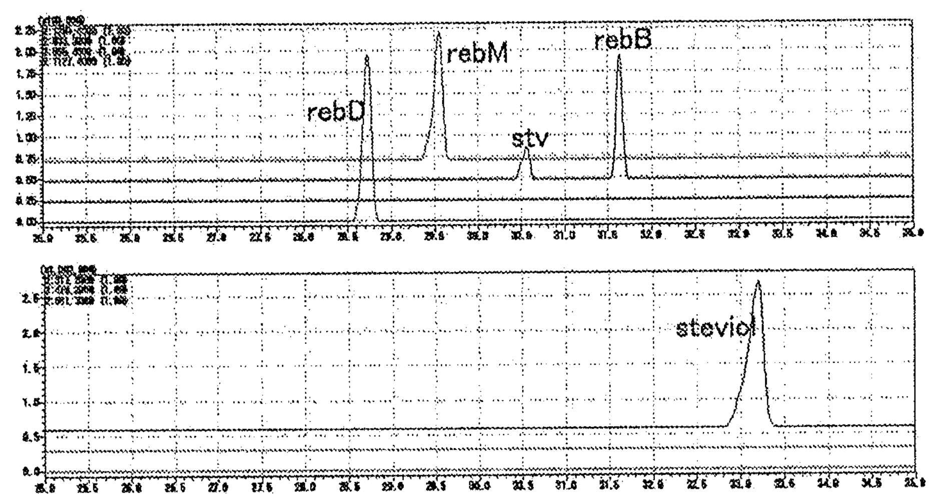
Figure 4A:
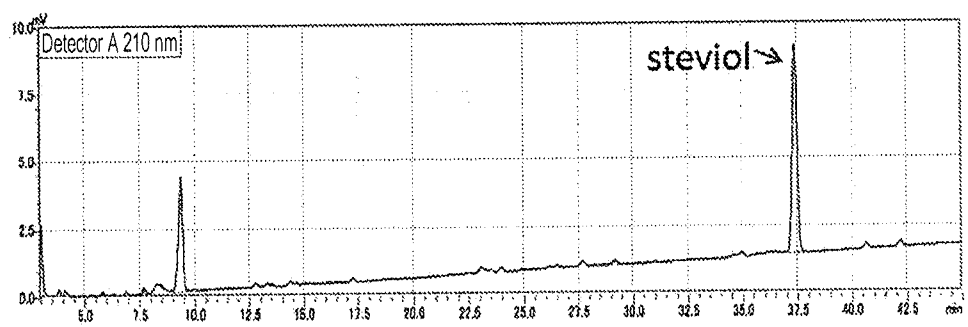
FIGS. 4A - 4B show HPLC analysis of a product using a BGL11 crude enzyme solution with rebD (0.05 mg/ml) as a substrate.
Figure 5A:
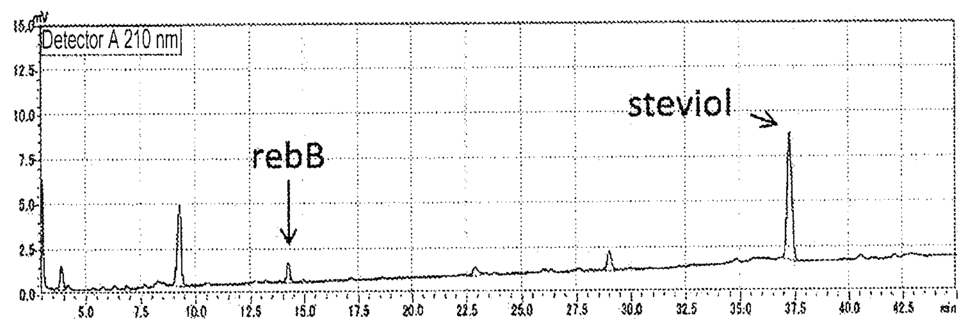
FIGS. 5A - 5B show HPLC analysis of a product using a BGL11 crude enzyme solution with rebA (0.05 mg/ml) as a substrate.

When rebM was used as the substrate, steviol was detected as a main product, and rebD, stv, and rebB were detected as intermediates (FIG. 3A). When rebD (FIG. 4A), rebA (FIG. 5A), stv, or rub was used as the substrate, the main product was also steviol.

The same reaction as above was also performed using C-1 crude enzyme solution as a control. However, none of the substrates were hydrolyzed, and no product was detected, which was considered to indicate that the above-described steviol glycoside-hydrolyzing activity was attributed to AOBGL11p.

Reaction Conditions (2)—Reaction Mixture Contains Acetonitrile—

Figure 3C:
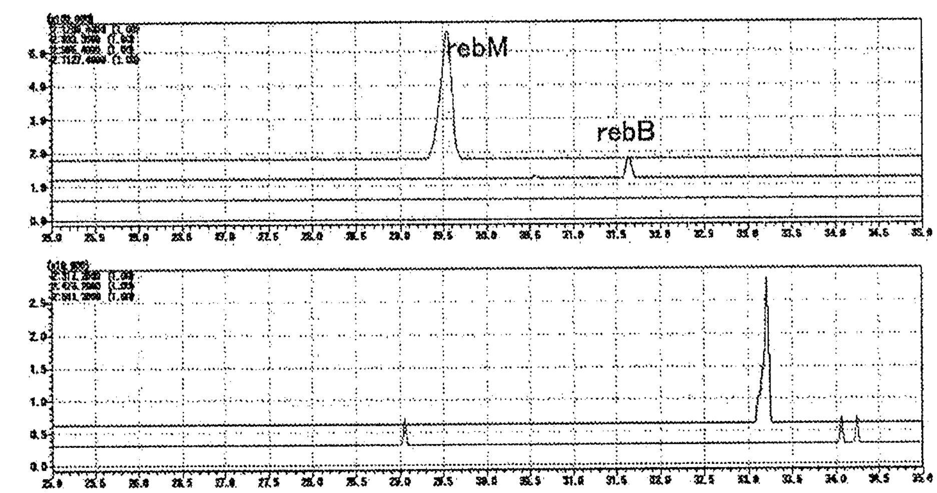
Figure 4B:
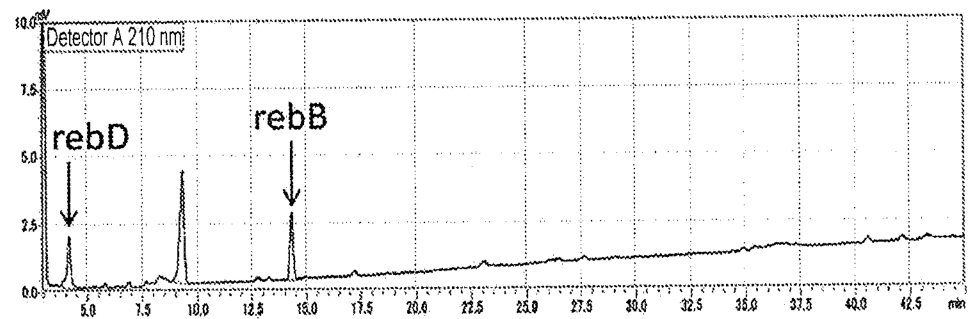
Figure 5B:
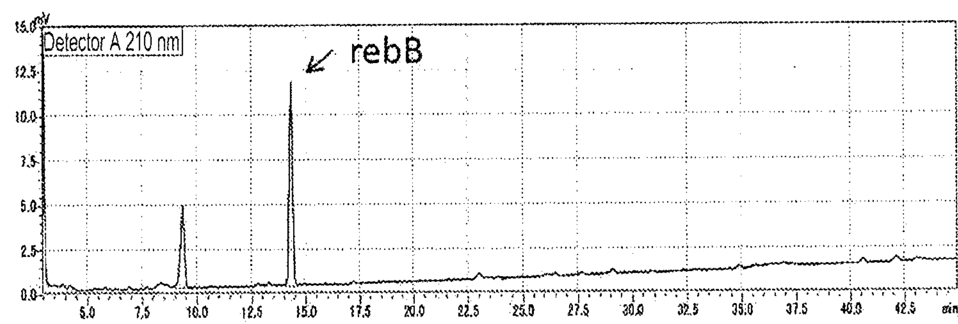

50 μg/ml of a substrate, 20 μl of the enzyme solution, 50 mM sodium phosphate buffer (pH 6.5), and 0% or 8% acetonitrile were mixed to a total volume of 100 μl, and the mixture was reacted at 37° C. for 24 hours. The reaction mixture was passed through Sep-Pak C18 (Waters) washed with acetonitrile and equilibrated with water. The reaction product was subsequently washed with 20% acetonitrile and then eluted with 50% acetonitrile. The eluate was evaporated to dryness with SpeedVac. The resulting product was dissolved in 100 μL of water, and the solution was subjected to HPLC.

rebM was rarely degraded in the reaction mixture supplemented with 8% acetonitrile (FIG. 3C).

rebD and rebA were hydrolyzed to form rebB, but no detectable steviol, even when 8% acetonitrile was added (FIGS. 4B and 5B).

stv was hydrolyzed to form steB, and the substrate was not detected in the reaction for 24 hours, even when 8% acetonitrile was added. steB was further hydrolyzed into steviol, albeit in a very small amount.

Rub was hydrolyzed by the reaction for 24 hours to form steviol. The substrate was not detected in the reaction for 24 hours.

Reaction Conditions (3)

50 μg/ml of a substrate, 20 μl of BGL11 crude enzyme solution (protein concentration: 6.5 mg/ml), and 50 mM sodium phosphate buffer (pH 6.5) were mixed to a total volume of 100 μl, and the mixture was reacted at 50° C. for 24 hours. The reaction mixture was passed through Sep-Pak C18 (Waters) washed with acetonitrile and equilibrated with water. The reaction product was subsequently washed with 20% acetonitrile and then eluted with 50% acetonitrile. The eluate was evaporated to dryness with SpeedVac. The resulting product was dissolved in 100 μL of water, and the solution was subjected to HPLC.

rebM was not hydrolyzed.

rebD and rebA were partially hydrolyzed to form rebB. However, no further hydrolyzed product was detected.

stv was partially hydrolyzed to form steB. However, no further hydrolyzed product was detected.

Rub was partially hydrolyzed to produce steM and steviol.

From these results, the hydrolysis reaction mediated by AOBGL11p was considered as follows:

(1) AOBGL11p hydrolyzes a steviol glycoside into steviol and is considered to hydrolyze sugars one by one from an intermediate product.

(2) AOBGL11p preferentially hydrolyzes a sugar added at the 19 position of steviol over a sugar added at the 13 position of steviol.

(3) A branched trisaccharide is not hydrolyzed depending on reaction conditions.

Hydrolysis of *Stevia rebaudiana* Extract

Figure 6A:
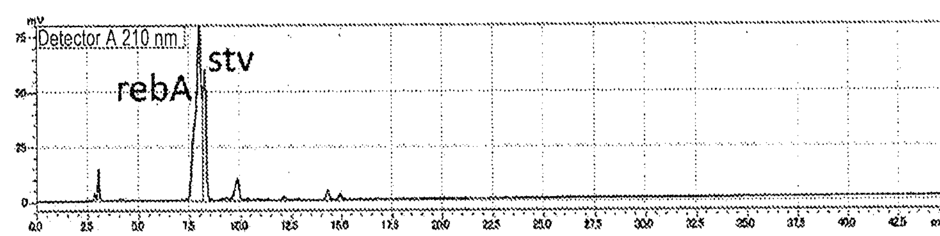
FIG. 6A shows HPLC analysis of Rebaudio JM.
Figure 6B:
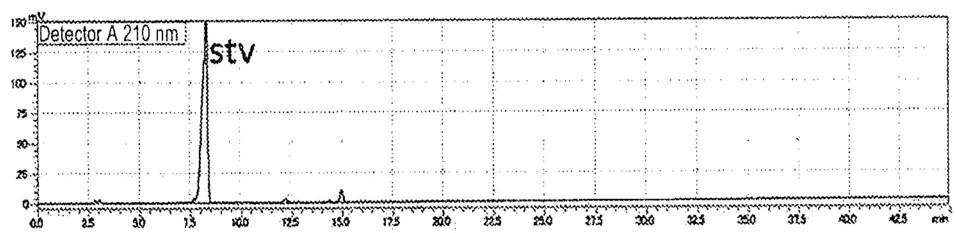
FIG. 6B shows HPLC analysis of Stevilon S-100.

Rebaudio JM (Morita Kagaku Kogyo Co., Ltd., FIG. 6A) and Stevilon S-100 (Morita Kagaku Kogyo Co., Ltd., FIG. 6B) were hydrolyzed with AOBGL11p.

Figure 7A:
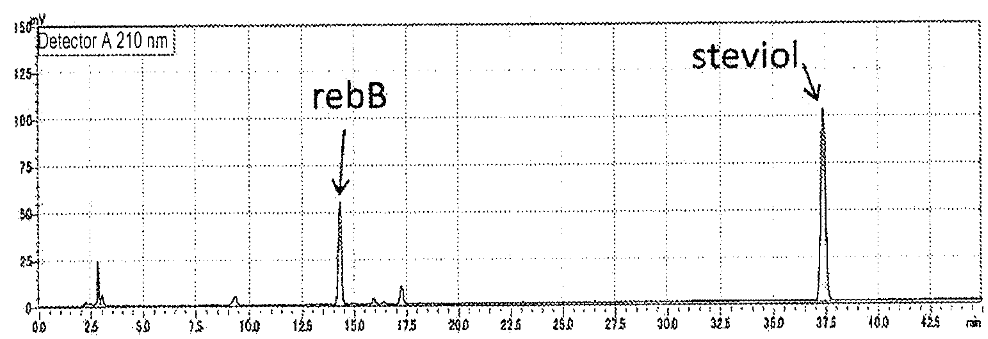
FIGS. 7A - 7C show HPLC analysis of a hydrolysate of Rebaudio JM (1 mg/ml).
Figure 7B:
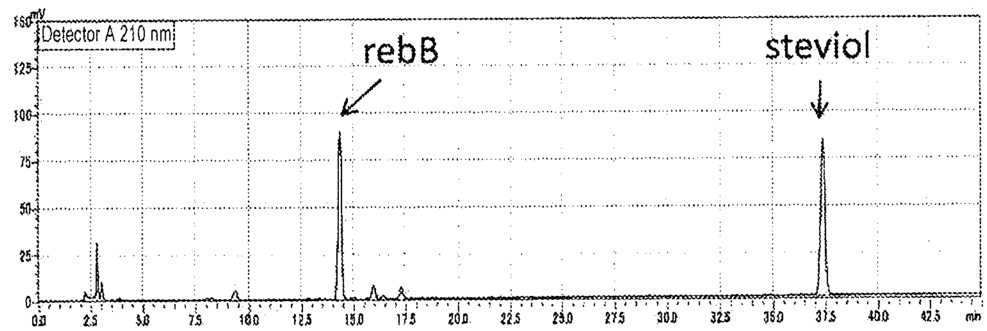
Figure 7C:
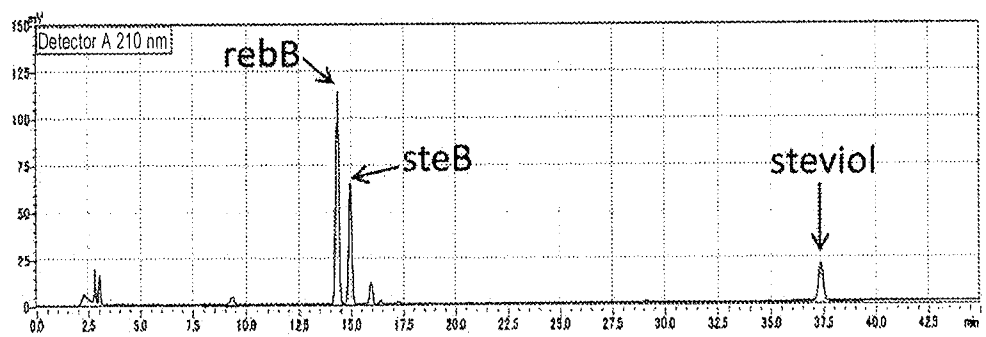
Figure 8A:
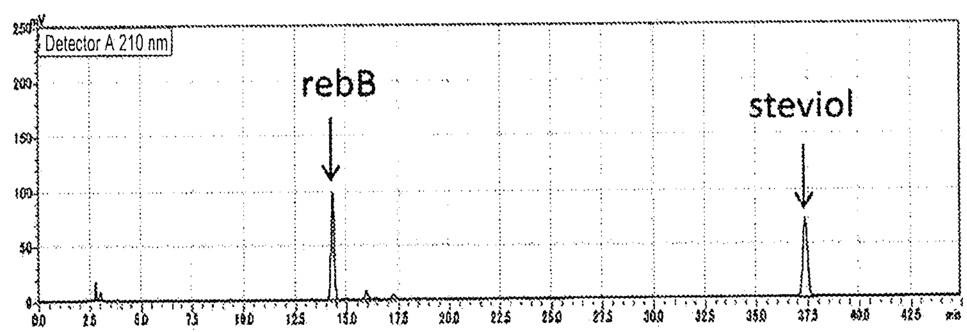
FIGS. 8A - 8C show HPLC analysis of a hydrolysate of Rebaudio JM (10 mg/ml).
Figure 8B:
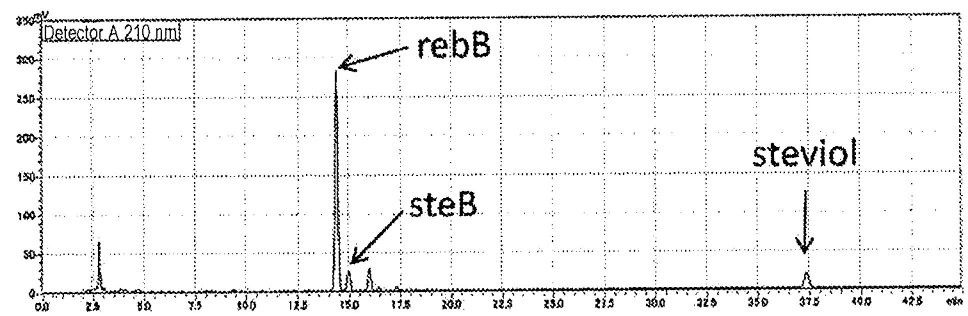
Figure 8C:
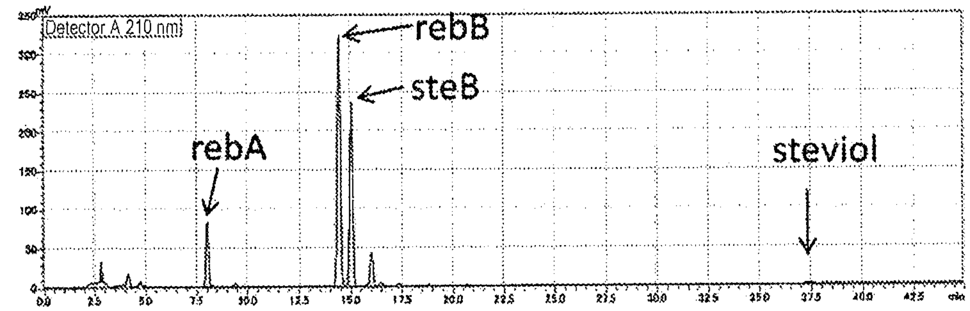
Figure 9A:
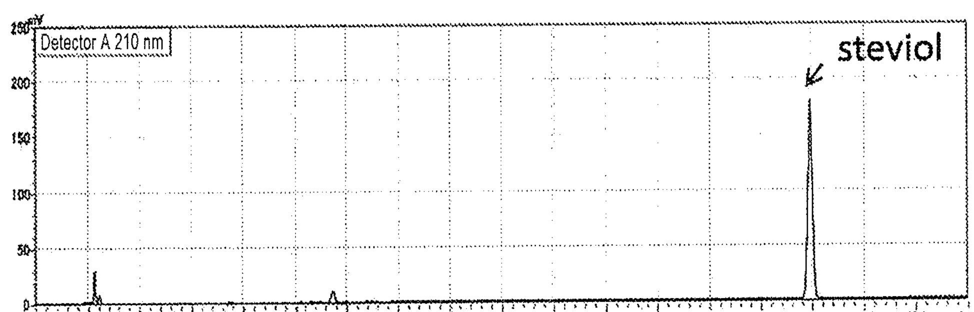
FIGS. 9A - 9C show results of analyzing a hydrolysate of Stevilon S-100 (1 mg/ml).
Figure 9B:
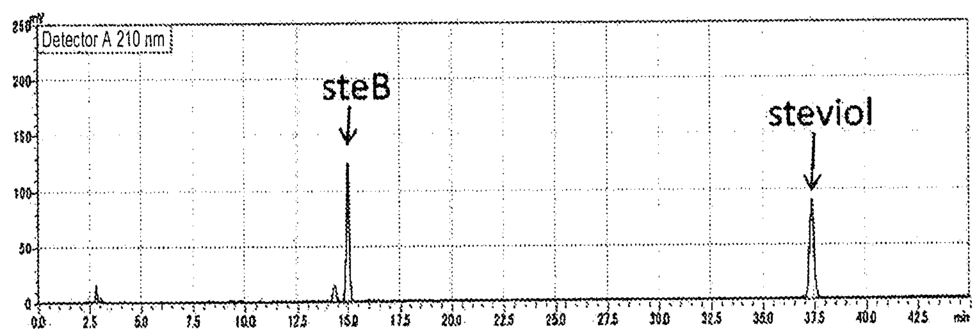
Figure 9C:
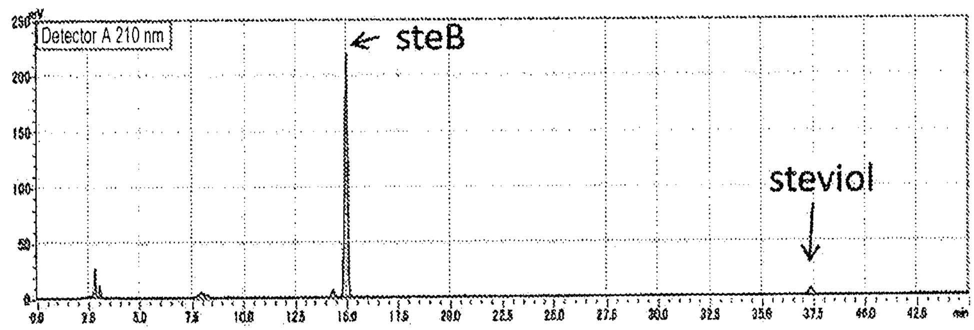

Under reaction conditions, 1 mg/ml (FIG. 8) or 10 mg/ml (FIG. 7) Rebaudio JM or 1 mg/ml Stevilon S-100 (FIG. 9), 20 μl of the enzyme solution, 50 mM sodium phosphate buffer (pH 6.5), and 0%, 4% or 8% acetonitrile were mixed to a total volume of 100 μl, and the mixture was reacted at 37° C. for 24 hours. The reaction mixture was passed through Sep-Pak C18 (Waters) washed with acetonitrile and equilibrated with water. The reaction product was subsequently washed with 20% acetonitrile and then eluted with 50% acetonitrile. The eluate was evaporated to dryness with SpeedVac. The resulting product was dissolved in 100 μL of water, and the solution was subjected to HPLC.

Cloning of cDNA of AOBGL11

Figure 10B:
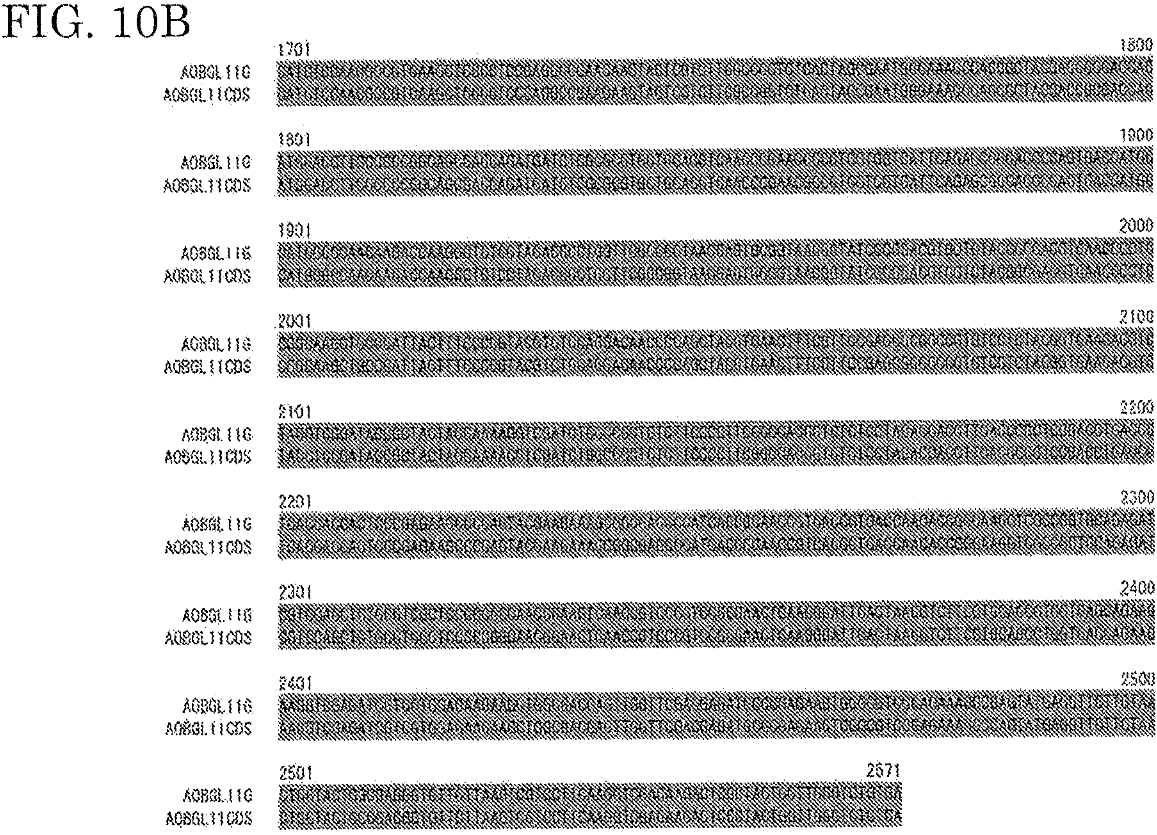
FIG. 10B shows the comparison between the genomic DNA sequence (AOBGL11G) (SEQ ID NO: 4) and the cDNA sequence (AOBGL11CDS) (SEQ ID NO: 3) of AOBGL11 (FIG. 10A continued).

BGL11-1 strain was cultured in 10 ml of a culture medium for enzyme production, and the cells were collected by filtration. The cells were frozen in liquid nitrogen and ground in a mortar, and total RNA was then extracted using RNeasy (QIAGEN). cDNA was synthesized using the SuperScript Double-Stranded cDNA Synthesis Kit (Life Technologies). Using this cDNA as a template, PCR was performed with the primers AOBGL11-F and AOBGL11-R, using KOD-Plus (Toyobo). About 2.52 kbp of the resulting DNA fragment was cloned as AOBGL11 cDNA using the Zero Blunt TOPO PCR cloning Kit (Invitrogen), thus obtaining a plasmid pCR-AOBGL11 cDNA. The nucleotide sequence was confirmed, and the CDS sequence was as shown in SEQ ID NO: 1. The comparison between the genomic DNA sequence and the CDS sequence of AOBGL11 is shown in FIG. 10.

Construction of Expression Vectors for Yeast and Transformation of Yeast

DNA fragment of about 2.52 kbp obtained by digesting the plasmid pCR-AOBGL11 cDNA with EcoRI was inserted into the EcoRI site of a yeast expression vector pYE22m (Biosci. Biotech. Biochem., 59, 1221-1228, 1995). Expression vector wherein AOBGL11 was inserted in an orientation so as to be expressed under the control of the GAPDH promoter of the vector pYE22m was selected and designated as pYE-AOBGL3c. *S. cerevisiae* strain EH13-15 (trp1, MATα) (Appl. Microbiol. Biotechnol., 30, 515-520, 1989) was used as the parental strain for transformation.

Each of the plasmids pYE22m (control) and pYE-AOBGL11 (for expression of AOBGL11) was used to transform strain EH13-15 in accordance with the lithium acetate method. A strain that grew on SC-Trp (containing, per liter, 6.7 g of Yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 0.6 g of uracil) agar medium (2% agar) was selected as the transformed strain.

The strain transformed with the plasmid pYE22m was designated as C-Y strain, and the strain transformed with the plasmid pYE-AOBGL11 was designated as AOBGL11-Y strain.

One platinum loop of the selected C-Y strain and AOBGL11-Y strain was inoculated to 10 mL of SC-Trp liquid medium supplemented with 1/10 volume of 1 M potassium phosphate buffer, and cultured with shaking at 30° C. and 125 rpm for 2 days. The resulting culture was separated into the culture supernatant and cells by centrifugation. The culture supernatant was concentrated by ultrafiltration through Amicon Ultra-15 50k (Merck), and the buffer was replaced with 50 mM sodium phosphate buffer (pH 7.0) containing 0.1% CHAPS to obtain about 1 ml of a culture supernatant concentrate.

The cells were suspended in 50 mM sodium phosphate buffer (pH 7.0) containing 0.1% CHAPS solution 1 ml and then homogenated with glass beads, and the supernatant obtained by centrifugation was used as the cell homogenate.

To 20 μl of the culture supernatant concentrate or cell homogenate, 1 μl of a solution of 2% X-β-Glc in DMF was added, and the mixture was reacted at room temperature for 5 minutes. As a result, only the AOBGL11-Y strain-derived cell homogenate was stained blue, suggesting that the strain had X-β-Glc activity.

pNP-β-Glc Activity Measurement pNP-β-Glc degrading activity was studied. 10 μL of the crude enzyme solution, 50 μL of a 0.2 M sodium phosphate buffer (pH 7.0), 50 μL of a 20 mM aqueous pNP-β-Glc solution, and water were mixed to a total volume of 200 ML, and the mixture was reacted at 37° C. Since BGL11-1 crude enzyme solution had high activity, the crude enzyme solution was diluted 100-fold with 50 mM sodium phosphate buffer (pH 7.0) containing 0.1% CHAPS and used. The change in absorbance at 405 nm (Δ405) per minute based on p-nitrophenol (pNP) liberated by the hydrolysis of pNP-β-Glc was 0.068 for the AOBGL11-Y crude enzyme solution and 0.000 for the C-Y crude enzyme solution.

Steviol Glycoside-Hydrolyzing Activity

Cell homogenates of C-Y strain and AOBGL11-Y strain were studied for the activity to hydrolyze steviol glycosides.

50 μg/ml of a substrate, 20 μl of the enzyme solution, and 50 mM sodium phosphate buffer (pH 6.0) were mixed to a total volume of 100 μl, and the mixture was reacted at 50° C. The reaction mixture was passed through Sep-Pak C18 (Waters) washed with acetonitrile and equilibrated with water. The reaction product was subsequently washed with 20% acetonitrile and then eluted with 50% acetonitrile. The eluate was evaporated to dryness with SpeedVac. The resulting product was dissolved in 100 μL of water, and the solution was subjected to HPLC.

No product of the reaction using the C-Y strain-derived cell homogenate was detected from any of the steviol glycosides.

On the other hand, the reaction using the AOBGL11-Y strain-derived cell homogenate yielded substrates and products shown below.

TABLE 4

| Substrate | Product |
|---|---|
| Rubusoside | Steviolmonoside, Steviol |
| Stevioside | Steviolbioside, Steviol |
| Rebaudioside A | Rebaudioside B, Steviol |
| Rebaudioside D | Rebaudioside B, Steviol |
| Rebaudioside M | Rebaudioside B, Steviol |

On the other hand, substrates and products shown in the table below were obtained by the addition of 8% acetonitrile into the reaction mixture.

TABLE 5

| Substrate | Product |
|---|---|
| Rubusoside | Steviolmonoside, Steviol |
| Stevioside | Steviolbioside |
| Rebaudioside A | Rebaudioside B |
| Rebaudioside D | Rebaudioside B |
| Rebaudioside M | Not detected |

These results indicated that when expressed in yeast, AOBGL11 exhibits activity equivalent to the case where AOBGL11 is expressed in koji mold.

Hydrolysis of Rebaudioside C (Steviol Glycoside Containing Rhamnose)

50 μg/ml of rebaudioside C (rebC), 20 μl of BGL11 crude enzyme solution, and 50 mM sodium phosphate buffer (pH 6.5) were mixed to a total volume of 100 μl, and the mixture was reacted at 37° C. for 24 hours. Each crude enzyme solution used was the crude enzyme solution having a protein concentration of 6.5 mg/ml (undiluted, C), the crude enzyme solution diluted 1/1000 (B), or the crude enzyme solution concentrated about 20-fold by ultrafiltration (C). The reaction mixture was passed through Sep-Pak C18 (Waters) washed with acetonitrile and equilibrated with water. The reaction product was subsequently washed with 20% acetonitrile and then eluted with 50% acetonitrile. The eluate was evaporated to dryness with SpeedVac. The resulting product was dissolved in 100 μL of water, and the solution was subjected to HPLC and LC-MS. The results are shown in FIG. 12.

When rebaudioside C was used as a substrate, two peaks were observed as hydrolysis products at RT of 16.2 minutes and RT of 17.5 minutes. From the relationship between enzyme levels and products, the product at RT of 16.2 minutes was considered to be first produced and further hydrolyzed to generate the product at RT of 17.5 minutes. Taken together with the results of LC-MS analysis, the peak at RT of 16.2 minutes was a steviol glycoside (2Glc+Rha) with m/z 787.4, but was not consistent with RT of dulcoside A. This peak was presumably steviol glycoside C (13 position: Rhaα1,2(Gluβ1,3)Glcβ1-, 19 position: H), also because BGL11 has the property of preferentially hydrolyzing a sugar added at the 19 position. On the other hand, the peak at RT of 17.5 minutes was a steviol glycoside (Glc+Rha) with m/z 625.3, which seemed to be a hydrolysate of steviol glycoside C. Therefore, this peak was presumably steviol glycoside A (13 position: Rhaα1,2Glcβ1-, 19 position: H). Neither steM or steE wherein one glucose was added to steviol nor the aglycone, steviol was detected, suggesting that BGL11 cannot hydrolyze rhamnoside bond.

Hydrolysis of Rebaudioside F (Steviol Glycoside Containing Xylose)

50 μg/ml of rebaudioside F (rebF), 20 μl of BGL11 crude enzyme solution (protein concentration: 6.5 mg/ml), and 50 mM sodium phosphate buffer (pH 6.5) were mixed to a total volume of 100 μl, and the mixture was reacted at 37° C. for 1 hour (FIG. 13B) or 24 hours (FIG. 13C). The reaction mixture was passed through Sep-Pak C18 (Waters) washed with acetonitrile and equilibrated with water. The reaction product was subsequently washed with 20% acetonitrile and then eluted with 50% acetonitrile. The eluate was evaporated to dryness with SpeedVac. The resulting product was dissolved in 100 μL of water, and the solution was subjected to HPLC and LC-MS. The results are shown in FIG. 13 and the table below.

TABLE 6

| Hydrolysis of Rebaudioside F* (LC-MS) | | | | | | | |
|---|---|---|---|---|---|---|---|
| m/z (negative) | 949.4 | 935.4 | 787.4 | 773.4 | 625.3 | 611.3 | 317.3 |
| Rt | 29.96 | 29.86 | 31.00 | 31.20 | 31.14 | 31.43 | 32.77 |
| compound | Reb C | Reb F | (2Glc + Rha) | (2Glc + Xly) | (Glc + Rha) | (Glc + Xly) | Steviol |
| Reb F std | 6,602,603 | 16,565,869 | 0 | 0 | 0 | 0 | 0 |
| Reb F digest 1 hr | 24,830 | 48,461 | 3,698,543 | 7,047,604 | 293,669 | 758,892 | 1,133,105 |
| Reb F digest 24 hr | 0 | 0 | 3,051,659 | 6,477,965 | 3,949,804 | 6,803,829 | 14,980,583 |

The results of analyzing only the substrate indicated that rebF coexisted with rebC. In the reaction for 1 hour, peaks at 16.2 minutes and 16.7 minutes (FIG. 13B) were observed as main hydrolysis products. In the reaction for 24 hours, the hydrolysis reaction further proceeded, and the generation of peaks at 17.5 minutes and 18.5 minutes (FIG. 13C) and the production of the aglycone, steviol were observed in addition to the above-described peaks. As a result of LC-MS, taken together with the results of rebC hydrolysis, the peaks at RT of 16.2 minutes and RT of 17.5 minutes were presumably steviol glycoside C (13 position: Rhaα1,2(Gluβ1,3)Glcβ1-, 19 position: H) and steviol glycoside A (13 position: Rhaα1,2Glcβ1-, 19 position: H), respectively. The peak at 16.7 minutes was a steviol glycoside (2Glc+Xly) with m/z 773.4. This was presumably steviol glycoside D (13 position: Xylβ1,2(Gluβ1,3)Glcβ1-, 19 position: H) because BGL11 preferentially hydrolyzes a sugar added at the 19 position. On the other hand, the peak at 18.5 minutes was m/z 611.3 (Glc+Xly), which seemed to be a hydrolysis product of steviol glycoside D. Therefore, this peak was presumably steviol glycoside B (13 position: Xylβ1, 2Glcβ1-, 19 position: H). As stated above, the production of steviol was also observed. In this hydrolysis experiment, BGL11 was unable to hydrolyze rebC into the aglycone, steviol and was therefore considered to hydrolyze rebF into the aglycone, steviol. This suggested that BGL11 can hydrolyze a xyloside bond.

The invention claimed is:

1. A method comprising reacting a protein comprising the amino acid sequence of SEQ ID NO: 2 with a first steviol glycoside.

2. The method according to claim 1, wherein the first steviol glycoside is selected from the group consisting of steviolmonoside, steviol monoglucosyl ester, rubusoside, steviolbioside, stevioside, rebaudioside B, rebaudioside A, rebaudioside C, rebaudioside D, rebaudioside E, rebaudioside F, rebaudioside M, dulcoside A, steviol glycoside B, steviol glycoside C, and steviol glycoside D.

3. The method according to claim 1, further comprising obtaining steviol and/or a second steviol glycoside, wherein the second steviol glycoside is different from the first steviol glycoside.

4. The method according to claim 3, wherein the second steviol glycoside is selected from the group consisting of steviolmonoside, steviolbioside, rebaudioside B, steviol glycoside A, steviol glycoside B, steviol glycoside C, and steviol glycoside D.

5. The method according to claim 1, wherein the reaction with the first steviol glycoside is performed in the presence of an organic solvent.

6. The method according to claim 5, wherein the organic solvent is acetonitrile.

7. The method according to claim 1, wherein a glucosyl ester bond at the 19 position or glycoside bond, except for rhamnoside bond, within a side chain at the 19 position of the first steviol glycoside is preferentially cleaved over glucoside bond at the 13 position or glycoside bond, except for rhamnoside bond, within a side chain at the 13 position thereof.

8. The method according to claim 1, wherein the first steviol glycoside is a steviol glycoside wherein a branched trisaccharide, disaccharide, or glucose monosaccharide is linked through glucoside bond to the 13 position, and/or a branched trisaccharide, disaccharide, or glucose monosaccharide is linked through a glucosyl ester bond to the 19 position, and wherein:

(1) glycoside bond, except for rhamnoside bond, within the disaccharide or the glucoside bond or glucosyl ester bond of the glucose monosaccharide is preferentially cleaved over the branched trisaccharide;

(2) glucose is preferentially cleaved when xylose and glucose, or rhamnose and glucose are further linked to glucose linked to aglycone;

(3) glycoside bond, except for rhamnoside bond, within the branched trisaccharide at the 19 position is preferentially cleaved over glycoside bond, except for rhamnoside bond, within the branched trisaccharide at the 13 position;

(4) glycoside bond, except for rhamnoside bond, within the branched trisaccharide or disaccharide at the 19 position and the glucosyl ester bond of the glucose monosaccharide at the 19 position is preferentially cleaved over glycoside bond, except for rhamnoside bond, within the disaccharide at the 13 position; and/or (5) the glucosyl ester bond of the glucose monosaccharide at the 19 position is preferentially cleaved over the glucoside bond of the glucose monosaccharide at the 13 position.

9. A method according to claim 1 wherein the protein is from a non-human transformed cell comprising a polynucleotide selected from the group consisting of polynucleotides (a) and (b) shown below:

(a) a polynucleotide comprising the nucleotide sequence of SEQ ID NO: 1;

(b) a polynucleotide encoding a protein comprising the amino acid sequence of SEQ ID NO: 2.

10. The method according to claim 9, wherein the polynucleotide is inserted into an expression vector.

11. The method according to claim 9, wherein the transformed cell is transformed koji mold, transformed yeast, a transformed bacterium, or a transformed plant.

12. A method comprising culturing a non-human transformant capable of producing a first steviol glycoside and comprising a polynucleotide selected from the group consisting of polynucleotides (a) and (b) shown below:

(a) a polynucleotide comprising the nucleotide sequence of SEQ ID NO: 1;

(b) a polynucleotide encoding a protein comprising the amino acid sequence of SEQ ID NO: 2.

13. The method according to claim 12, wherein the polynucleotide is inserted into an expression vector.

14. The method according to claim 12, wherein the transformant is transformed koji mold, transformed yeast, a transformed bacterium or a transformed plant.

15. A reaction mixture comprising (1) a steviol glycoside and (2)(i) a protein comprising the amino acid sequence of SEQ ID NO: 2 and/or (ii) an extract or a homogenate of a non-human transformant as defined in claim 12.

* * * * *

SEQUENCE LISTING

```
<160> NUMBER OF SEQ ID NOS: 8

<210> SEQ ID NO 1
<211> LENGTH: 2517
<212> TYPE: DNA
<213> ORGANISM: Aspergillus oryzae var.Brunneus
<220> FEATURE:
<221> NAME/KEY: CDS
<222> LOCATION: (1)..(2517)

<400> SEQUENCE: 1

atg cct cgt cta gac gtc gag aag acc atc gaa gaa ctc tcc cta ggg       48
Met Pro Arg Leu Asp Val Glu Lys Thr Ile Glu Glu Leu Ser Leu Gly
1               5                   10                  15

gag aag gtc gcc ttg acg gcc gga atc gac ttc tgg cac aca gct tcc       96
Glu Lys Val Ala Leu Thr Ala Gly Ile Asp Phe Trp His Thr Ala Ser
            20                  25                  30

gtg ccc cgc ctc aac atc cca act ctc cgc atg tcc gat ggc ccc aac      144
Val Pro Arg Leu Asn Ile Pro Thr Leu Arg Met Ser Asp Gly Pro Asn
        35                  40                  45

ggc gtg cgc gga act cgc ttc ttc aac ggc gtc cca gcc gca tgt ttc      192
Gly Val Arg Gly Thr Arg Phe Phe Asn Gly Val Pro Ala Ala Cys Phe
    50                  55                  60

cct tgt gcc acg gca ctg ggc gca acc tgg gac acc gag ctg ctc cat      240
Pro Cys Ala Thr Ala Leu Gly Ala Thr Trp Asp Thr Glu Leu Leu His
65                  70                  75                  80

gag att ggt caa ttg atg gga gag gaa tcc att gcc aag ggc tcg cac      288
Glu Ile Gly Gln Leu Met Gly Glu Glu Ser Ile Ala Lys Gly Ser His
                85                  90                  95

att att cta ggc ccc acg atc aac acc cag cgg tct ccg ctc gga ggt      336
Ile Ile Leu Gly Pro Thr Ile Asn Thr Gln Arg Ser Pro Leu Gly Gly
            100                 105                 110

cgt gga ttc gag tcc ttt gct gag gac ggt gtg ctc tct gga ctc ttg      384
Arg Gly Phe Glu Ser Phe Ala Glu Asp Gly Val Leu Ser Gly Leu Leu
        115                 120                 125
```

```
gcc ggt tat atc tcc aag ggt att cag gag aag ggc gtt gcg gcc act      432
Ala Gly Tyr Ile Ser Lys Gly Ile Gln Glu Lys Gly Val Ala Ala Thr
    130                 135                 140

ctg aag cac ttt gtg tgc aat gac cag gag cat cag cgt atg gct gtt      480
Leu Lys His Phe Val Cys Asn Asp Gln Glu His Gln Arg Met Ala Val
145                 150                 155                 160

gat agc att gtt acg cag cgg gct ctg cgc gag atc tat ttg ttg ccg      528
Asp Ser Ile Val Thr Gln Arg Ala Leu Arg Glu Ile Tyr Leu Leu Pro
                165                 170                 175

ttt caa ttg gcc atg agg att tgc agg acg gct tgt gtt atg aca gct      576
Phe Gln Leu Ala Met Arg Ile Cys Arg Thr Ala Cys Val Met Thr Ala
            180                 185                 190

tat aac aag gtg aat gga acg cac gtt agt cag aat aag gaa atc atc      624
Tyr Asn Lys Val Asn Gly Thr His Val Ser Gln Asn Lys Glu Ile Ile
        195                 200                 205

acg gat atc ttg cgg aag gag tgg gga tgg gat ggg ttg gtt atg agt      672
Thr Asp Ile Leu Arg Lys Glu Trp Gly Trp Asp Gly Leu Val Met Ser
    210                 215                 220

gat tgg ttc ggt acc tac agt acc agt gat gca atc aat gct ggt ttg      720
Asp Trp Phe Gly Thr Tyr Ser Thr Ser Asp Ala Ile Asn Ala Gly Leu
225                 230                 235                 240

gac ctg gag atg ccg ggc aag aca cgc tgg cgt gga act gct ctg gcg      768
Asp Leu Glu Met Pro Gly Lys Thr Arg Trp Arg Gly Thr Ala Leu Ala
                245                 250                 255

cat gcc gtt tct tcg aac gag gtc gct gag ttt gtc atg gat gag cgt      816
His Ala Val Ser Ser Asn Glu Val Ala Glu Phe Val Met Asp Glu Arg
            260                 265                 270

gtc cgc aat gtg ttg aac ctg gtt aac ttt gtg gat ggc ctg aac atc      864
Val Arg Asn Val Leu Asn Leu Val Asn Phe Val Asp Gly Leu Asn Ile
        275                 280                 285

ccg gag aac gcc ccg gag aag gct ctc aac cgg cca cag gac caa gct      912
Pro Glu Asn Ala Pro Glu Lys Ala Leu Asn Arg Pro Gln Asp Gln Ala
    290                 295                 300

ctt ctc cgc cgt gct gcg gcg gag tct gtc gtt ctc atg aag aac gag      960
Leu Leu Arg Arg Ala Ala Ala Glu Ser Val Val Leu Met Lys Asn Glu
305                 310                 315                 320

gaa gac atc ttg ccc ctg aag aag gag aag tct atc ttg gtt att ggt     1008
Glu Asp Ile Leu Pro Leu Lys Lys Glu Lys Ser Ile Leu Val Ile Gly
                325                 330                 335

cct aac tcc aag gtt gcg gcg tac tgc ggc ggt gga tcc gcg tct ttg     1056
Pro Asn Ser Lys Val Ala Ala Tyr Cys Gly Gly Gly Ser Ala Ser Leu
            340                 345                 350

gat gct tat tac act gtc acc cca ttc gag ggt gtc tcg gct cag agc     1104
Asp Ala Tyr Tyr Thr Val Thr Pro Phe Glu Gly Val Ser Ala Gln Ser
        355                 360                 365

aag ggt gag gtc aag ttc tct caa ggt gtc tat tcg cac aag gac ctt     1152
Lys Gly Glu Val Lys Phe Ser Gln Gly Val Tyr Ser His Lys Asp Leu
    370                 375                 380

cct ctc ctt gga ccc ctg ctg aag acc gcc gac ggc aag act ggt ttc     1200
Pro Leu Leu Gly Pro Leu Leu Lys Thr Ala Asp Gly Lys Thr Gly Phe
385                 390                 395                 400

tca ttc aag gta tac aac gag cac cct tcc gag tct aac cgc gaa ctt     1248
Ser Phe Lys Val Tyr Asn Glu His Pro Ser Glu Ser Asn Arg Glu Leu
                405                 410                 415

atc gag cag ctg cac ctg gtc tcg tcg agc gga ttc cta atg gac tat     1296
Ile Glu Gln Leu His Leu Val Ser Ser Ser Gly Phe Leu Met Asp Tyr
            420                 425                 430

gtc aac ccc aag atc aag tct ctc acc tac tac gtc gac atg gag ggt     1344
Val Asn Pro Lys Ile Lys Ser Leu Thr Tyr Tyr Val Asp Met Glu Gly
        435                 440                 445
```

```
ctc ttc acc ccc gag gaa gac ggt gtc tac gac ttc ggt gtc act gtt      1392
Leu Phe Thr Pro Glu Glu Asp Gly Val Tyr Asp Phe Gly Val Thr Val
    450                 455                 460

gtt ggc acc ggc caa ctg ttc atc gac ggc gag ctc gtc gtt gac aac      1440
Val Gly Thr Gly Gln Leu Phe Ile Asp Gly Glu Leu Val Val Asp Asn
465                 470                 475                 480

acc aag aac cag cgc cag ggc tcc gcc ttc ttc ggc tcc gct acc gtc      1488
Thr Lys Asn Gln Arg Gln Gly Ser Ala Phe Phe Gly Ser Ala Thr Val
                485                 490                 495

gaa gag aag ggc tcc aaa gaa ctc aag gcc ggc caa aca tac aag gtt      1536
Glu Glu Lys Gly Ser Lys Glu Leu Lys Ala Gly Gln Thr Tyr Lys Val
            500                 505                 510

ctc ttc cag ttc ggc aca gcc cct acc tcc gac ctc gat acc cgc ggc      1584
Leu Phe Gln Phe Gly Thr Ala Pro Thr Ser Asp Leu Asp Thr Arg Gly
        515                 520                 525

gtg gta gtc ttc gga ccc ggt ggc ttc cgc ttc gga gcc agc cgt cgc      1632
Val Val Val Phe Gly Pro Gly Gly Phe Arg Phe Gly Ala Ser Arg Arg
    530                 535                 540

gtc ggc cag gaa gag ctc atc tcc aac gcc gtc aag ctc gcc tcc gag      1680
Val Gly Gln Glu Glu Leu Ile Ser Asn Ala Val Lys Leu Ala Ser Glu
545                 550                 555                 560

gcc gaa caa gta gtc gtc ttc gcc ggt ctg act agc gaa tgg gaa acc      1728
Ala Glu Gln Val Val Val Phe Ala Gly Leu Thr Ser Glu Trp Glu Thr
                565                 570                 575

gag ggc tac gac cgc gac cac atg gac ctt ccc ccc ggc agc gac gag      1776
Glu Gly Tyr Asp Arg Asp His Met Asp Leu Pro Pro Gly Ser Asp Glu
            580                 585                 590

atg atc tcg cgc gtg ctg gac gtc aac ccg aac gcc gtc gtg gtc att      1824
Met Ile Ser Arg Val Leu Asp Val Asn Pro Asn Ala Val Val Val Ile
        595                 600                 605

cag agc ggc acc cca gtg acc atg cca tgg gcc aac aag acc aag gct      1872
Gln Ser Gly Thr Pro Val Thr Met Pro Trp Ala Asn Lys Thr Lys Ala
    610                 615                 620

ctc cta cac gcc tgg ttc ggc ggt aac gag tgc ggt aac ggt atc gcg      1920
Leu Leu His Ala Trp Phe Gly Gly Asn Glu Cys Gly Asn Gly Ile Ala
625                 630                 635                 640

gac gtg ctc tac ggc gac gtc aac ccc tcc ggc aag ctg ccc att act      1968
Asp Val Leu Tyr Gly Asp Val Asn Pro Ser Gly Lys Leu Pro Ile Thr
                645                 650                 655

ttc ccc gta cgt ctg cag gac aac ccc agc tac gtc aac ttt cgt tcc      2016
Phe Pro Val Arg Leu Gln Asp Asn Pro Ser Tyr Val Asn Phe Arg Ser
            660                 665                 670

gag cgc ggc cgt gtc ctc tac ggt gaa gac gtc tac gtc gga tac cgc      2064
Glu Arg Gly Arg Val Leu Tyr Gly Glu Asp Val Tyr Val Gly Tyr Arg
        675                 680                 685

tac tac gaa aag gtc gat ctg gcc cct ctc ttc ccc ttc ggc cac ggt      2112
Tyr Tyr Glu Lys Val Asp Leu Ala Pro Leu Phe Pro Phe Gly His Gly
    690                 695                 700

ctc tcc tac acc acc ttc acc cgc tcc gac ctg acc ctc acc acc act      2160
Leu Ser Tyr Thr Thr Phe Thr Arg Ser Asp Leu Thr Leu Thr Thr Thr
705                 710                 715                 720

ccc gag aag ccc cag tac gaa gaa agc ggc gag ccc atc acc gca acc      2208
Pro Glu Lys Pro Gln Tyr Glu Glu Ser Gly Glu Pro Ile Thr Ala Thr
                725                 730                 735

gtc acg gtg acc aac acc ggc aag gtc gcc ggt gca gag atc gtc cag      2256
Val Thr Val Thr Asn Thr Gly Lys Val Ala Gly Ala Glu Ile Val Gln
            740                 745                 750

ctc tgg gtc gct ccc ccg gca acg gaa gtc aac cgt ccc gtc cgc gaa      2304
Leu Trp Val Ala Pro Pro Ala Thr Glu Val Asn Arg Pro Val Arg Glu
```

```
        755                 760                 765

ctc aag gga ttc act aag gtc ttc ctg cag cct ggt gag cag aag aag     2352
Leu Lys Gly Phe Thr Lys Val Phe Leu Gln Pro Gly Glu Gln Lys Lys
    770                 775                 780

gtc gag atc gtc gtg gag aag aag ctg gcg acg agt tgg ttc gac gag     2400
Val Glu Ile Val Val Glu Lys Lys Leu Ala Thr Ser Trp Phe Asp Glu
785                 790                 795                 800

atg cgc gag aag tgg gcg tcc gag aaa ggc gag tat gag gtt ctt gta     2448
Met Arg Glu Lys Trp Ala Ser Glu Lys Gly Glu Tyr Glu Val Leu Val
                805                 810                 815

act ggt act ggc gag ggt gtt ctt aag tcg tcc ttc aag gtc gag aag     2496
Thr Gly Thr Gly Glu Gly Val Leu Lys Ser Ser Phe Lys Val Glu Lys
            820                 825                 830

act cgc tac tgg ttg ggt ctg                                         2517
Thr Arg Tyr Trp Leu Gly Leu
        835


<210> SEQ ID NO 2
<211> LENGTH: 839
<212> TYPE: PRT
<213> ORGANISM: Aspergillus oryzae var.Brunneus

<400> SEQUENCE: 2

Met Pro Arg Leu Asp Val Glu Lys Thr Ile Glu Glu Leu Ser Leu Gly
1               5                   10                  15

Glu Lys Val Ala Leu Thr Ala Gly Ile Asp Phe Trp His Thr Ala Ser
            20                  25                  30

Val Pro Arg Leu Asn Ile Pro Thr Leu Arg Met Ser Asp Gly Pro Asn
        35                  40                  45

Gly Val Arg Gly Thr Arg Phe Phe Asn Gly Val Pro Ala Ala Cys Phe
    50                  55                  60

Pro Cys Ala Thr Ala Leu Gly Ala Thr Trp Asp Thr Glu Leu Leu His
65                  70                  75                  80

Glu Ile Gly Gln Leu Met Gly Glu Glu Ser Ile Ala Lys Gly Ser His
                85                  90                  95

Ile Ile Leu Gly Pro Thr Ile Asn Thr Gln Arg Ser Pro Leu Gly Gly
            100                 105                 110

Arg Gly Phe Glu Ser Phe Ala Glu Asp Gly Val Leu Ser Gly Leu Leu
        115                 120                 125

Ala Gly Tyr Ile Ser Lys Gly Ile Gln Glu Lys Gly Val Ala Ala Thr
    130                 135                 140

Leu Lys His Phe Val Cys Asn Asp Gln Glu His Gln Arg Met Ala Val
145                 150                 155                 160

Asp Ser Ile Val Thr Gln Arg Ala Leu Arg Glu Ile Tyr Leu Leu Pro
                165                 170                 175

Phe Gln Leu Ala Met Arg Ile Cys Arg Thr Ala Cys Val Met Thr Ala
            180                 185                 190

Tyr Asn Lys Val Asn Gly Thr His Val Ser Gln Asn Lys Glu Ile Ile
        195                 200                 205

Thr Asp Ile Leu Arg Lys Glu Trp Gly Trp Asp Gly Leu Val Met Ser
    210                 215                 220

Asp Trp Phe Gly Thr Tyr Ser Thr Ser Asp Ala Ile Asn Ala Gly Leu
225                 230                 235                 240

Asp Leu Glu Met Pro Gly Lys Thr Arg Trp Arg Gly Thr Ala Leu Ala
                245                 250                 255

His Ala Val Ser Ser Asn Glu Val Ala Glu Phe Val Met Asp Glu Arg
```

```
            260                 265                 270

Val Arg Asn Val Leu Asn Leu Val Asn Phe Val Asp Gly Leu Asn Ile
        275                 280                 285

Pro Glu Asn Ala Pro Glu Lys Ala Leu Asn Arg Pro Gln Asp Gln Ala
    290                 295                 300

Leu Leu Arg Arg Ala Ala Ala Glu Ser Val Val Leu Met Lys Asn Glu
305                 310                 315                 320

Glu Asp Ile Leu Pro Leu Lys Lys Glu Lys Ser Ile Leu Val Ile Gly
                325                 330                 335

Pro Asn Ser Lys Val Ala Ala Tyr Cys Gly Gly Gly Ser Ala Ser Leu
            340                 345                 350

Asp Ala Tyr Tyr Thr Val Thr Pro Phe Glu Gly Val Ser Ala Gln Ser
        355                 360                 365

Lys Gly Glu Val Lys Phe Ser Gln Gly Val Tyr Ser His Lys Asp Leu
    370                 375                 380

Pro Leu Leu Gly Pro Leu Leu Lys Thr Ala Asp Gly Lys Thr Gly Phe
385                 390                 395                 400

Ser Phe Lys Val Tyr Asn Glu His Pro Ser Glu Ser Asn Arg Glu Leu
                405                 410                 415

Ile Glu Gln Leu His Leu Val Ser Ser Ser Gly Phe Leu Met Asp Tyr
            420                 425                 430

Val Asn Pro Lys Ile Lys Ser Leu Thr Tyr Tyr Val Asp Met Glu Gly
        435                 440                 445

Leu Phe Thr Pro Glu Glu Asp Gly Val Tyr Asp Phe Gly Val Thr Val
    450                 455                 460

Val Gly Thr Gly Gln Leu Phe Ile Asp Gly Glu Leu Val Val Asp Asn
465                 470                 475                 480

Thr Lys Asn Gln Arg Gln Gly Ser Ala Phe Phe Gly Ser Ala Thr Val
                485                 490                 495

Glu Glu Lys Gly Ser Lys Glu Leu Lys Ala Gly Gln Thr Tyr Lys Val
            500                 505                 510

Leu Phe Gln Phe Gly Thr Ala Pro Thr Ser Asp Leu Asp Thr Arg Gly
        515                 520                 525

Val Val Val Phe Gly Pro Gly Gly Phe Arg Phe Gly Ala Ser Arg Arg
    530                 535                 540

Val Gly Gln Glu Glu Leu Ile Ser Asn Ala Val Lys Leu Ala Ser Glu
545                 550                 555                 560

Ala Glu Gln Val Val Val Phe Ala Gly Leu Thr Ser Glu Trp Glu Thr
                565                 570                 575

Glu Gly Tyr Asp Arg Asp His Met Asp Leu Pro Pro Gly Ser Asp Glu
            580                 585                 590

Met Ile Ser Arg Val Leu Asp Val Asn Pro Asn Ala Val Val Val Ile
        595                 600                 605

Gln Ser Gly Thr Pro Val Thr Met Pro Trp Ala Asn Lys Thr Lys Ala
    610                 615                 620

Leu Leu His Ala Trp Phe Gly Gly Asn Glu Cys Gly Asn Gly Ile Ala
625                 630                 635                 640

Asp Val Leu Tyr Gly Asp Val Asn Pro Ser Gly Lys Leu Pro Ile Thr
                645                 650                 655

Phe Pro Val Arg Leu Gln Asp Asn Pro Ser Tyr Val Asn Phe Arg Ser
            660                 665                 670

Glu Arg Gly Arg Val Leu Tyr Gly Glu Asp Val Tyr Val Gly Tyr Arg
        675                 680                 685
```

```
Tyr Tyr Glu Lys Val Asp Leu Ala Pro Leu Phe Pro Phe Gly His Gly
    690                 695                 700

Leu Ser Tyr Thr Thr Phe Thr Arg Ser Asp Leu Thr Leu Thr Thr Thr
705                 710                 715                 720

Pro Glu Lys Pro Gln Tyr Glu Glu Ser Gly Glu Pro Ile Thr Ala Thr
                725                 730                 735

Val Thr Val Thr Asn Thr Gly Lys Val Ala Gly Ala Glu Ile Val Gln
            740                 745                 750

Leu Trp Val Ala Pro Pro Ala Thr Glu Val Asn Arg Pro Val Arg Glu
        755                 760                 765

Leu Lys Gly Phe Thr Lys Val Phe Leu Gln Pro Gly Glu Gln Lys Lys
    770                 775                 780

Val Glu Ile Val Val Glu Lys Lys Leu Ala Thr Ser Trp Phe Asp Glu
785                 790                 795                 800

Met Arg Glu Lys Trp Ala Ser Glu Lys Gly Glu Tyr Glu Val Leu Val
                805                 810                 815

Thr Gly Thr Gly Glu Gly Val Leu Lys Ser Ser Phe Lys Val Glu Lys
            820                 825                 830

Thr Arg Tyr Trp Leu Gly Leu
        835


<210> SEQ ID NO 3
<211> LENGTH: 2520
<212> TYPE: DNA
<213> ORGANISM: Aspergillus oryzae var.Brunneus

<400> SEQUENCE: 3

atgcctcgtc tagacgtcga gaagaccatc gaagaactct ccctagggga gaaggtcgcc      60

ttgacggccg gaatcgactt ctggcacaca gcttccgtgc cccgcctcaa catcccaact     120

ctccgcatgt ccgatggccc caacggcgtg cgcggaactc gcttcttcaa cggcgtccca     180

gccgcatgtt tcccttgtgc cacggcactg ggcgcaacct gggacaccga gctgctccat     240

gagattggtc aattgatggg agaggaatcc attgccaagg gctcgcacat tattctaggc     300

cccacgatca acacccagcg gtctccgctc ggaggtcgtg gattcgagtc ctttgctgag     360

gacggtgtgc tctctggact cttggccggt tatatctcca agggtattca ggagaagggc     420

gttgcggcca ctctgaagca ctttgtgtgc aatgaccagg agcatcagcg tatggctgtt     480

gatagcattg ttacgcagcg ggctctgcgc gagatctatt tgttgccgtt tcaattggcc     540

atgaggattt gcaggacggc ttgtgttatg acagcttata acaaggtgaa tggaacgcac     600

gttagtcaga ataaggaaat catcacggat atcttgcgga aggagtgggg atgggatggg     660

ttggttatga gtgattggtt cggtacctac agtaccagtg atgcaatcaa tgctggtttg     720

gacctggaga tgccgggcaa gacacgctgg cgtggaactg ctctggcgca tgccgtttct     780

tcgaacgagg tcgctgagtt tgtcatggat gagcgtgtcc gcaatgtgtt gaacctggtt     840

aactttgtgg atggcctgaa catcccggag aacgccccgg agaaggctct caaccggcca     900

caggaccaag ctcttctccg ccgtgctgcg gcggagtctg tcgttctcat gaagaacgag     960

gaagacatct tgcccctgaa gaaggagaag tctatcttgg ttattggtcc taactccaag    1020

gttgcggcgt actgcggcgg tggatccgcg tctttggatg cttattacac tgtcacccca    1080

ttcgagggtg tctcggctca gagcaagggt gaggtcaagt tctctcaagg tgtctattcg    1140

cacaaggacc ttcctctcct tggacccctg ctgaagaccg ccgacggcaa gactggtttc    1200
```

```
tcattcaagg tatacaacga gcacccttcc gagtctaacc gcgaacttat cgagcagctg   1260
cacctggtct cgtcgagcgg attcctaatg gactatgtca accccaagat caagtctctc   1320
acctactacg tcgacatgga gggtctcttc acccccgagg aagacggtgt ctacgacttc   1380
ggtgtcactg ttgttggcac cggccaactg ttcatcgacg gcgagctcgt cgttgacaac   1440
accaagaacc agcgccaggg ctccgccttc ttcggctccg ctaccgtcga agagaagggc   1500
tccaaagaac tcaaggccgg ccaaacatac aaggttctct tccagttcgg cacagcccct   1560
acctccgacc tcgatacccg cggcgtggta gtcttcggac ccggtggctt ccgcttcgga   1620
gccagccgtc gcgtcggcca ggaagagctc atctccaacg ccgtcaagct cgcctccgag   1680
gccgaacaag tagtcgtctt cgccggtctg actagcgaat gggaaaccga gggctacgac   1740
cgcgaccaca tggaccttcc ccccggcagc gacgagatga tctcgcgcgt gctggacgtc   1800
aacccgaacg ccgtcgtggt cattcagagc ggcaccccag tgaccatgcc atgggccaac   1860
aagaccaagg ctctcctaca cgcctggttc ggcggtaacg agtgcggtaa cggtatcgcg   1920
gacgtgctct acggcgacgt caacccctcc ggcaagctgc ccattacttt ccccgtacgt   1980
ctgcaggaca accccagcta cgtcaacttt cgttccgagc gcggccgtgt cctctacggt   2040
gaagacgtct acgtcggata ccgctactac gaaaaggtcg atctggcccc tctcttcccc   2100
ttcggccacg gtctctccta caccaccttc acccgctccg acctgaccct caccaccact   2160
cccgagaagc cccagtacga agaaagcggc gagcccatca ccgcaaccgt cacggtgacc   2220
aacaccggca aggtcgccgg tgcagagatc gtccagctct gggtcgctcc cccggcaacg   2280
gaagtcaacc gtcccgtccg cgaactcaag ggattcacta aggtcttcct gcagcctggt   2340
gagcagaaga aggtcgagat cgtcgtggag aagaagctgg cgacgagttg gttcgacgag   2400
atgcgcgaga agtgggcgtc cgagaaaggc gagtatgagg ttcttgtaac tggtactggc   2460
gagggtgttc ttaagtcgtc cttcaaggtc gagaagactc gctactggtt gggtctgtga   2520
```

<210> SEQ ID NO 4
<211> LENGTH: 2571
<212> TYPE: DNA
<213> ORGANISM: Aspergillus oryzae var.Brunneus

<400> SEQUENCE: 4

```
atgcctcgtc tagacgtcga gaagaccatc gaagaactct ccctagggga gaaggtcgcc     60
ttgacggccg gtaagtcaaa aacccacgat cgcaagagaa aagaaatgct aagaatccca    120
ggaatcgact tctggcacac agcttccgtg ccccgcctca acatcccaac tctccgcatg    180
tccgatggcc ccaacggcgt gcgcggaact cgcttcttca acggcgtccc agccgcatgt    240
ttcccttgtg ccacggcact gggcgcaacc tgggacaccg agctgctcca tgagattggt    300
caattgatgg gagaggaatc cattgccaag ggctcgcaca ttattctagg ccccacgatc    360
aacacccagc ggtctccgct cggaggtcgt ggattcgagt cctttgctga ggacggtgtg    420
ctctctggac tcttggccgg ttatatctcc aagggtattc aggagaaggg cgttgcggcc    480
actctgaagc actttgtgtg caatgaccag gagcatcagc gtatggctgt tgatagcatt    540
gttacgcagc gggctctgcg cgagatctat ttgttgccgt ttcaattggc catgaggatt    600
tgcaggacgg cttgtgttat gacagcttat aacaaggtga atggaacgca cgttagtcag    660
aataaggaaa tcatcacgga tatcttgcgg aaggagtggg gatgggatgg gttggttatg    720
agtgattggt tcggtaccta cagtaccagt gatgcaatca atgctggttt ggacctggag    780
atgccgggca agacacgctg gcgtggaact gctctggcgc atgccgtttc ttcgaacgag    840
```

```
gtcgctgagt ttgtcatgga tgagcgtgtc cgcaatgtgt tgaacctggt taactttgtg    900
gatggcctga acatcccgga gaacgccccg gagaaggctc tcaaccggcc acaggaccaa    960
gctcttctcc gccgtgctgc ggcggagtct gtcgttctca tgaagaacga ggaagacatc   1020
ttgcccctga agaaggagaa gtctatcttg gttattggtc ctaactccaa ggttgcggcg   1080
tactgcggcg gtggatccgc gtctttggat gcttattaca ctgtcacccc attcgagggt   1140
gtctcggctc agagcaaggg tgaggtcaag ttctctcaag gtgtctattc gcacaaggac   1200
cttcctctcc ttggacccct gctgaagacc gccgacggca agactggttt ctcattcaag   1260
gtatacaacg agcacccttc cgagtctaac cgcgaactta tcgagcagct gcacctggtc   1320
tcgtcgagcg gattcctaat ggactatgtc aaccccaaga tcaagtctct cacctactac   1380
gtcgacatgg agggtctctt cacccccgag gaagacggtg tctacgactt cggtgtcact   1440
gttgttggca ccggccaact gttcatcgac ggcgagctcg tcgttgacaa caccaagaac   1500
cagcgccagg gctccgcctt cttcggctcc gctaccgtcg aagagaaggg ctccaaagaa   1560
ctcaaggccg gccaaacata caaggttctc ttccagttcg gcacagcccc tacctccgac   1620
ctcgataccc gcggcgtggt agtcttcgga cccggtggct tccgcttcgg agccagccgt   1680
cgcgtcggcc aggaagagct catctccaac gccgtcaagc tcgcctccga ggccgaacaa   1740
gtagtcgtct tcgccggtct gactagcgaa tgggaaaccg agggctacga ccgcgaccac   1800
atggaccttc cccccggcag cgacgagatg atctcgcgcg tgctggacgt caacccgaac   1860
gccgtcgtgg tcattcagag cggcacccca gtgaccatgc catgggccaa caagaccaag   1920
gctctcctac acgcctggtt cggcggtaac gagtgcggta acggtatcgc ggacgtgctc   1980
tacggcgacg tcaacccctc cggcaagctg cccattactt tccccgtacg tctgcaggac   2040
aaccccagct acgtcaactt tcgttccgag cgcggccgtg tcctctacgg tgaagacgtc   2100
tacgtcggat accgctacta cgaaaaggtc gatctggccc ctctcttccc cttcggccac   2160
ggtctctcct acaccacctt cacccgctcc gacctgaccc tcaccaccac tcccgagaag   2220
ccccagtacg aagaaagcgg cgagcccatc accgcaaccg tcacggtgac caacaccggc   2280
aaggtcgccg gtgcagagat cgtccagctc tgggtcgctc cccggcaac ggaagtcaac    2340
cgtcccgtcc gcgaactcaa gggattcact aaggtcttcc tgcagcctgg tgagcagaag   2400
aaggtcgaga tcgtcgtgga gaagaagctg gcgacgagtt ggttcgacga gatgcgcgag   2460
aagtgggcgt ccgagaaagg cgagtatgag gttcttgtaa ctggtactgg cgagggtgtt   2520
cttaagtcgt ccttcaaggt cgagaagact cgctactggt tgggtctgtg a            2571
```

<210> SEQ ID NO 5
<211> LENGTH: 779
<212> TYPE: PRT
<213> ORGANISM: Aspergillus oryzae var.Brunneus

<400> SEQUENCE: 5

```
Met Val Ser Gly Val Phe Thr Lys Gly Val Leu Leu Leu Gly Leu Leu
1               5                   10                  15

Ser Gly Leu Ala Leu Gly Gln Asp Glu Lys Pro Arg Tyr Lys Asp Pro
            20                  25                  30

Ser Val Pro Val Glu Glu Arg Val Thr Asp Leu Leu Gly Arg Met Thr
        35                  40                  45

Leu Glu Glu Lys Met Ser Gln Leu Ile Gln Gly Asp Ile Thr Asn Trp
    50                  55                  60
```

```
Met Asn Glu Thr Thr Gly Glu Phe Asn Leu Thr Gly Leu Glu Trp Ser
65                  70                  75                  80

Thr Lys Met Arg Gly Gly Met Phe Tyr Val Gly Tyr Pro Val Pro Trp
                85                  90                  95

Asp Tyr Ile Ala Asp Asn Val Lys Lys Ala Gln Asp Tyr Ile Leu Gln
            100                 105                 110

Asn Thr Thr Leu Gly Ile Pro Ala Ile Val Gln Thr Glu Ser Leu His
        115                 120                 125

Gly Phe Leu Ile Gly Asn Ala Thr Ile Tyr Asn Ser Pro Ile Gly Phe
    130                 135                 140

Ala Cys Ser Phe Asn Pro Glu Leu Ile Glu Lys Met Ala Arg Leu Ile
145                 150                 155                 160

Gly Gln Glu Ala Ser Ala Leu Gly Val Asn His Val Met Gly Pro Val
                165                 170                 175

Val Asp Leu Ala Arg Glu Leu Arg Phe Gly Arg Val Glu Glu Thr Tyr
            180                 185                 190

Gly Glu Asp Pro Phe Leu Ala Gly Glu Ile Gly Tyr His Tyr Thr Lys
        195                 200                 205

Gly Ile Gln Ser His Asn Ile Ser Ala Asn Val Lys His Phe Val Gly
    210                 215                 220

Phe Ser Gln Pro Glu Gln Gly Leu Asn Thr Ala Pro Val His Gly Gly
225                 230                 235                 240

Glu Arg Tyr Leu Arg Thr Thr Trp Leu Pro Ser Phe Lys Arg Ala Ile
                245                 250                 255

Met Asp Ala Gly Ala Trp Ser Ile Met Ser Ala Tyr His Ser Tyr Asp
            260                 265                 270

Gly Ile Pro Ala Val Ala Asp Tyr His Thr Leu Thr Glu Ile Leu Arg
        275                 280                 285

Glu Glu Trp Gly Tyr Lys Tyr Trp Val Thr Ser Asp Ala Gly Ala Ser
    290                 295                 300

Asp Arg Val Cys Thr Ala Phe Lys Leu Cys Arg Ala Asp Pro Ile Asp
305                 310                 315                 320

Lys Glu Ala Val Thr Leu Ala Ile Leu Pro Ala Gly Asn Asp Val Glu
                325                 330                 335

Met Gly Gly Gly Ser Tyr Asn Phe Glu Thr Ile Ile Asp Leu Val Asn
            340                 345                 350

Ala Gly Lys Leu Asp Ile Glu Ile Val Asn Thr Ala Val Ser Arg Val
        355                 360                 365

Leu Arg Ala Lys Phe Glu Met Gly Leu Phe Glu Asn Pro Tyr Asn Ala
    370                 375                 380

Ala Pro Ala Ser Glu Trp Asn Lys Leu Ile His Thr Gln Glu Ala Val
385                 390                 395                 400

Asp Leu Ala Arg Glu Leu Asp Arg Glu Ser Ile Val Leu Leu Glu Asn
                405                 410                 415

His Asp Asn Ala Leu Pro Leu Lys Lys Ser Gly Ser Ile Ala Val Ile
            420                 425                 430

Gly Pro Met Ala His Gly Phe Met Asn Tyr Gly Asp Tyr Val Val Tyr
        435                 440                 445

Glu Ser Gln Tyr Arg Gly Val Thr Pro Leu Asp Gly Ile Lys Ala Ala
    450                 455                 460

Val Gly Asp Lys Ala Thr Ile Asn Tyr Ala Gln Gly Cys Glu Arg Trp
465                 470                 475                 480

Ser Asn Asp Gln Ser Gly Phe Ala Glu Ala Val Glu Ala Ala Lys Lys
```

```
                485                 490                 495

Ser Asp Val Ala Val Val Val Val Gly Thr Trp Ser Arg Asp Gln Lys
            500                 505                 510

Glu Leu Trp Ala Gly Leu Asn Ala Thr Thr Gly Glu His Val Asp Val
        515                 520                 525

Asn Ser Leu Ser Leu Val Gly Ala Gln Ala Pro Leu Ile Lys Ala Ile
    530                 535                 540

Ile Asp Thr Gly Val Pro Thr Val Val Val Leu Ser Ser Gly Lys Pro
545                 550                 555                 560

Ile Thr Glu Pro Trp Leu Ser Asn Asn Thr Ala Ala Leu Val Gln Gln
                565                 570                 575

Phe Tyr Pro Ser Glu Gln Gly Gly Asn Ala Leu Ala Asp Val Leu Phe
            580                 585                 590

Gly Asp Tyr Asn Pro Ser Gly Lys Leu Ser Val Ser Phe Pro His Ser
        595                 600                 605

Val Gly Asp Leu Pro Ile Tyr Tyr Asp Tyr Leu Asn Ser Ala Arg Glu
    610                 615                 620

Ile Gly Asp Ala Gly Tyr Ile Tyr Ser Asn Gly Thr Leu Glu Phe Gly
625                 630                 635                 640

His Gln Tyr Ala Leu Gly Asn Pro Lys Ala Trp Tyr Pro Phe Gly Tyr
                645                 650                 655

Gly Lys Ser Tyr Ser Ser Phe Glu Tyr Gly Ala Val Lys Leu Asp Lys
            660                 665                 670

Thr Asn Val Thr Glu Ala Asp Thr Val Thr Val Ser Val Asp Val Lys
        675                 680                 685

Asn Thr Asp Ala Thr Arg Glu Gly Thr Glu Val Val Gln Val Tyr Val
    690                 695                 700

Val Asp Glu Val Ala Ser Val Val Val Pro Asn Arg Leu Leu Lys Gly
705                 710                 715                 720

Phe Lys Lys Val Val Ile Pro Ala Gly Gln Thr Lys Thr Val Glu Ile
                725                 730                 735

Pro Leu Lys Val Gln Asp Leu Gly Leu Trp Asn Val Arg Met Lys Tyr
            740                 745                 750

Val Val Glu Pro Gly Ala Phe Gly Val Leu Val Gly Ser Ser Ser Glu
        755                 760                 765

Asp Ile Arg Gly Asn Ala Thr Phe Tyr Val Gln
    770                 775


<210> SEQ ID NO 6
<211> LENGTH: 861
<212> TYPE: PRT
<213> ORGANISM: Aspergillus oryzae var.Brunneus

<400> SEQUENCE: 6

Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80
```

```
Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
        275                 280                 285

Val Gly Ala Ala Leu Ala Gly Leu Asp Met Ser Met Pro Gly Asp Val
    290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
                325                 330                 335

Arg Ile Met Ala Ala Tyr Tyr Lys Val Gly Arg Asp Thr Lys Tyr Thr
            340                 345                 350

Pro Pro Asn Phe Ser Ser Trp Thr Arg Asp Glu Tyr Gly Phe Ala His
        355                 360                 365

Asn His Val Ser Glu Gly Ala Tyr Glu Arg Val Asn Glu Phe Val Asp
    370                 375                 380

Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
            420                 425                 430

Ala Asn Gly Cys Asp Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Ala Arg Gln
                485                 490                 495

Ala Ser Val Ser Leu Val Phe Val Asn Ser Asp Ser Gly Glu Gly Tyr
```

```
            500                 505                 510

Leu Ser Val Asp Gly Asn Glu Gly Asp Arg Asn Asn Ile Thr Leu Trp
        515                 520                 525

Lys Asn Gly Asp Asn Val Val Lys Thr Ala Ala Asn Asn Cys Asn Asn
    530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
        595                 600                 605

Gly Ser Pro Leu Val Lys Asp Ala Asn Asn Gly Asn Gly Ala Pro Gln
    610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
        675                 680                 685

Ile Gly Asp Ala Ser Glu Tyr Val Tyr Pro Glu Gly Leu Glu Arg Ile
    690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
        755                 760                 765

Lys Val Lys Asn Thr Gly Asn Val Ala Gly Asp Glu Val Pro Gln Leu
    770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
        835                 840                 845

Arg Lys Leu Pro Leu Gln Ala Ser Leu Pro Lys Ala Gln
    850                 855                 860
```

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
atgcctcgtc tagacgtcga gaa 23

-continued

```
<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8

tcacagaccc aaccagtagc ga                                    22
```